US009539176B2

(12) United States Patent
Funke et al.

(10) Patent No.: US 9,539,176 B2
(45) Date of Patent: Jan. 10, 2017

(54) PROCESS FOR MANUFACTURING A PHARMACEUTICAL DOSAGE FORM COMPRISING NIFEDIPINE AND CANDESARTAN CILEXETIL

(71) Applicant: BAYER PHARMA AKTIENGESELLSCHAFT, Berlin (DE)

(72) Inventors: Adrian Funke, Berlin (DE); Günter Meyer, Berlin (DE); Martina Smikalla, Düsseldorf (DE); Andreas Meeners, Nettetal (DE); Markus Wirges, Düsseldorf (DE); Daniela Brock, Mettmann (DE); Sarah Just, Pulheim (DE); Peter Kleinebudde, Düsseldorf (DE); Klaus Knop, Langenfeld (DE); Jochen Axel Zeitler, Cambridge (DE); Rolf-Anton Boeggering, Kaarst (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 13/889,100

(22) Filed: May 7, 2013

(65) Prior Publication Data
US 2013/0309302 A1 Nov. 21, 2013

(30) Foreign Application Priority Data

May 7, 2012 (EP) ..................................... 12167035
Jan. 18, 2013 (EP) ..................................... 13151946

(51) Int. Cl.
*A61J 3/00* (2006.01)
*A61K 31/4184* (2006.01)
(Continued)

(52) U.S. Cl.
CPC ........ *A61J 3/005* (2013.01); *A61J 3/06* (2013.01); *A61K 9/0004* (2013.01); *A61K 9/209* (2013.01);
(Continued)

(58) Field of Classification Search
CPC combination set(s) only.
See application file for complete search history.

(56) References Cited

U.S. PATENT DOCUMENTS

| 3,485,847 A | 12/1969 | Bossert et al. |
| 3,644,627 A | 2/1972 | Bossert et al. |

(Continued)

FOREIGN PATENT DOCUMENTS

| EP | 0459136 | 12/1991 |
| EP | 0459136 A1 | 12/1991 |

(Continued)

OTHER PUBLICATIONS

Cui et al., "Influence of the Composition of Water/Acetone Mixtures of Polymorphic Transformation of Candesartan Cilexetil", http://www.aidic.it/isic18/webpapers/19Cui.pdf, accessed Sep. 17, 2014.*

(Continued)

*Primary Examiner* — Bethany Barham
*Assistant Examiner* — Barbara Frazier
(74) *Attorney, Agent, or Firm* — Aseem Mehta

(57) ABSTRACT

The present invention relates to manufacturing processes for the preparation of a pharmaceutical dosage form comprising nifedipine and candesartan cilexetil and optionally at least one diuretic characterized in that nifedipine is released in the body in a controlled (modified) manner and the candesartan cilexetil is released rapidly (immediate release (IR)) and optionally the diuretic is released rapidly (immediate release (IR)) and the pharmaceutical dosage forms obtainable by these processes.

13 Claims, 9 Drawing Sheets

(51) Int. Cl.
  A61K 31/4418 (2006.01)
  A61K 31/4422 (2006.01)
  A61K 9/00 (2006.01)
  A61K 9/24 (2006.01)
  A61K 9/28 (2006.01)
  A61J 3/06 (2006.01)
(52) U.S. Cl.
  CPC ......... *A61K 9/2893* (2013.01); *A61K 31/4184* (2013.01); *A61K 31/4418* (2013.01); *A61K 31/4422* (2013.01)

(56) References Cited

U.S. PATENT DOCUMENTS

| | | | |
|---|---|---|---|
| 4,327,725 | A | 5/1982 | Cortese et al. |
| 4,576,604 | A | 3/1986 | Guittard et al. |
| 4,612,008 | A | 9/1986 | Wong et al. |
| 4,765,989 | A | 8/1988 | Wong et al. |
| 4,783,337 | A | 11/1988 | Wong et al. |
| 4,892,741 | A | 1/1990 | Ohm et al. |
| 4,931,285 | A | 6/1990 | Edgren et al. |
| 4,948,592 | A | 8/1990 | Ayer et al. |
| 5,082,668 | A | 1/1992 | Wong et al. |
| 5,160,744 | A | 11/1992 | Jao et al. |
| 5,178,867 | A | 1/1993 | Guittard et al. |
| 5,196,444 | A | 3/1993 | Naka et al. |
| 5,204,121 | A | 4/1993 | Bücheler et al. |
| 5,543,154 | A | 8/1996 | Rork et al. |
| 5,656,650 | A | 8/1997 | Weinstock |
| 6,294,201 | B1 | 9/2001 | Kettelhoit et al. |
| 6,555,136 | B2 | 4/2003 | Midha |
| 8,153,160 | B2 | 4/2012 | Ohm et al. |
| 2003/0161882 | A1 | 8/2003 | Waterman |
| 2004/0115134 | A1 | 6/2004 | Merisko-Liversidge |
| 2005/0008702 | A1 | 1/2005 | Faour et al. |
| 2005/0214373 | A1 | 9/2005 | Desai et al. |
| 2005/0266080 | A1 | 12/2005 | Desai et al. |
| 2007/0026065 | A1 | 2/2007 | Benke et al. |
| 2007/0082055 | A1 | 4/2007 | Kurgan et al. |
| 2010/0041644 | A1 | 2/2010 | Sanchez et al. |
| 2012/0034272 | A1 | 2/2012 | Kuhl et al. |

FOREIGN PATENT DOCUMENTS

| | | | |
|---|---|---|---|
| EP | 1306088 A1 | 6/1994 | |
| EP | 0753301 B1 | 7/1994 | |
| EP | 077660 | 4/1997 | |
| EP | 1024793 | 8/2000 | |
| EP | 1413315 | 4/2004 | |
| GB | 1173862 | 12/1969 | |
| GB | 2140687 | 12/1984 | |
| IE | 56515 | 5/1983 | |
| WO | 92/10097 | 6/1992 | |
| WO | 93/00071 | 1/1993 | |
| WO | 93/03711 | 3/1993 | |
| WO | 99/21535 | 5/1999 | |
| WO | 03035039 | 5/2003 | |
| WO | 03080057 | 10/2003 | |
| WO | 03097045 | 11/2003 | |
| WO | 2005009412 | 2/2005 | |
| WO | 2005070398 A2 | 8/2005 | |
| WO | 2005079751 A2 | 9/2005 | |
| WO | 2005084648 A1 | 9/2005 | |
| WO | 2007/003330 | 1/2007 | |
| WO | 2008044862 | 4/2008 | |
| WO | 2008045006 A1 | 4/2008 | |
| WO | 200803560 A2 | 6/2008 | |
| WO | 2009054550 A2 | 4/2009 | |
| WO | WO 2010/060564 * | 6/2010 | ............... A61K 9/28 |
| WO | 2012031124 A2 | 3/2012 | |

OTHER PUBLICATIONS

Müller et al., "Feasibility of Raman spectroscopy as PAT tool in active coating," Drug Dev. Ind. Pharm., 2010, 36 (2):234-243.

Romero-Torres et al., "Raman spectroscopic measurement of tablet-to-tablet coating variability," J. Pharm. Biomed. Analysis, 2005, 38(2):270-274.

Turton et al., "Challenges in the modeling and prediction of coating of pharmaceutical dosage forms," Powder Tech. 2008, 181(2):186-194.

Ekneet Sahni et al., "Experiments and numerical modeling to estimate the coating variability in a pan coater," Int. J. Pharm. 2011, 418(2)286:296.

Kandela et al., "Study of tablet coating parameters for a pan coater through video imaging and Monte Carlo simulation," Powder Tech. 2010, 204(1),103-112.

Rege et al., "Identification of critical process variables for coating actives onto tablets via statistically designed experiments," Int. J. Pharm., 2002, 237(1-2):87-94.

U.S. Appl. No. 13/130,294, 371(c) date Sep. 16, 2011.

Hayashi et al., "Disparate Effects of Calcium Antagonists on Renal Microcirculation," Hypertens. Res., 1996, 19:31-36.

Jamerson et al., "Benazepril plus Amlodipine or Hydroxhlorothiazide for Hypertension in High-Risk Patients," N. Engl. J. Med. 2008, 359(23):2417-2428.

Lippold, B.C., "Controlled Release Products: Approaches of Pharmaceutical Technology," Düsseldor, Wiss. Veri. Ges., 1989, 39-57.

Santus et al., "Osmotic Drug Delivery: A Review of the Patent Literature," Journal of Controlled Release, 1995, 35:1-21.

Verma et al., "Osmotically Controlled Oral Drug Delivery," Drug Development & Industrial Pharmacology 2000, 26(7): 695-708.

Verma et al., "Formulation Aspects in the Development of Osmotically Controlled Oral Drug Delivery Systems," Journal of Controlled Release 2002, 79:7-27.

Verma et al., "Osmotic Pumps in Drug Delivery," Crit. Rev. in Therapeutic Drug Carrier Systems 2004, 21(6):477-520.

Kubo et al., "Nonpeptide Angiotensin II Receptor Antagonists: Synthesis and Biological Activity of Potential Prodrugs of Benzimidazole-7-carboxylic Acids," Med. Chem. 1993, 36(16):2343-2349.

Hasabe et al., "Controlled-release nifedipine and candesartan low-dose combination therapy in patients with essential hypertentions: The NICE combi (Nifedipine and Candesartan Combination) Study," J. of Hypertension, 2005, 23 (2):445-453.

Wang et al., "An evaluation of process parameters to improve coating efficiency of an active tablet film-coating process," International Journal of Pharmaceutics, 2012, 427:163-169.

Zeitler et al., "Terahertz pulsed spectroscopy and imaging in the pharmaceutical setting—a review," Journal of Pharmacy and Pharmacology, 2007, 59:209-223.

Ho et al, "Analysis of sustained-release tablet film coats using terahertz pulsed imaging," Journal of Controlled Release, 2007, 119:253-261.

Ho et al., "Monitoring the Film Coating Unit Operation and Predicting Drug Dissolution Using Terahertz Pulsed Imaging," Journal of Pharm. Sciences, 2009, 98:4866-4876.

May et al., "Terahertz In-Line Sensor for Direct Coating ThicknessMeasurement of Individual Tablets During Film Coating in Real-Time," Journal of Pharm. Sciences, 2011, 100:1535-1544.

De Beer et al., "Near infrared and Raman spectroscopy for the in-process monitoring of pharmaceutical production processes," International Journal of Pharmaceutics, 2011, 417:32-47.

Gendre et al., "Development of a Process Analytical Technology (PAT) for in-line monitoringof film thickness and mass of coating materials during a pan coating operation." European Journal of Pharm. Sciences, 2011, 43:244-250.

Gendre et al., "Real-time predictions of drug release and end point detection of a coating operation by in-line near infrared measurements," International Journal of Pharmaceutics, 2011, 421:237-243.

Müller et al., "Prediction of dissolution time and coating thickness of sustained release formulations using Raman spectroscopy and terahertz pulsed imaging," European Journal of Pharmaceutics and Biopharmaceutics, 2012, 80:690-697.

Müller et al., "Validation of Raman spectroscopic procedures in agreement with ICH guideline Q2 with considering the transfer to real time monitoring of an active coating process," Journal of

(56) References Cited

OTHER PUBLICATIONS

Pharmaceutical and biomedical Analysis, 2010, 53:884-894.

Chen et al., "Modeling of Pan Coating Processes: Prediction of Tablet Content Uniformity and Determination of Critical Process Parameters," Journal of Pharm. Sciences, 2010, 99(7):3213-3222.

European Pharmacopoeia 8.0, "Uniformity of Dosage Units," Apr. 2012, section 2.9.40, pp. 357-359.

Bogomolov et al., "In-line analysis of a fluid bed pellet coating process using a combination of near infrared and Raman spectroscopy," J. Chemometrics, 2010, 24:544-557.

Fevotte et al., "In situ Raman spectroscopy for in-line control of pharmaceutical crystallization and solids elaboration process: a review," Trans ICemE, Part A, Chemical Engineering Research and Design, 2007, 85(A6): 906-920.

May et al., "Terahertz in-line sensor for direct coating thickness measurement of individual tablets during film coating in real-time," J Pharma Sci, Apr. 2011, 100(4) 1535-1544.

Gordon et al., "Raman mapping of pharmaceuticals," International Journal of Pharmaceuticals, 2011, 417:151-162.

Vankeirsbilck et al., "Applications of Raman spectroscopy in pharmaceutical analysis," Trends in Analytical Chemistry, 2002, 21(12): 869-877.

Notice of Opposition filed against Costa Rican patent application No. 2014-0511, Dec. 4, 2014, with English translation.

Third Party Observation filed before the Patent Office of Guatemala against Guatemala Application No. A2014-000245 (Translation), Feb. 24, 2016, 6 pages.

Desai, et al., "Pharmaceutical Development Fundamentals: Formulation design, challenges, and development considerations for fixed dose combination (FDC) of oral solid dosage forms", Pharmaceutical Development and Technology, 2012; 1-12.

Kim, et al., "Investigation of an active film coating to prepare new fixed-dose combination tablets for treatment of diabetes", Int. J. Pharm. 427(2), 2012, pp. 201-208.

Desai, et al., "Pharmaceutical Development Fundamentals: Formulation design, challenges, and development considerations for fixed dose combination (FDC) of oral solid dosage forms", Pharmaceutical Development and Technology, 2013; 18(6): 1265-1276.

"First Examination Report", New Zealand Application No. 700692, Feb. 26, 2016, 4 Pages.

L. B. Bohle, "Innovative 1", https://www.lbbohle.de/images/presse/innovative/en/bohle-innovativ_1-2012-EN.pdf, Feb. 9, 2012.

\* cited by examiner

PROCESS FOR MANUFACTURING A PHARMACEUTICAL DOSAGE FORM COMPRISING NIFEDIPINE AND CANDESARTAN CILEXETIL

BACKGROUND

The present invention relates to manufacturing processes for the preparation of a pharmaceutical dosage form comprising nifedipine and candesartan cilexetil and optionally at least one diuretic characterized in that nifedipine is released in the body in a controlled (modified) manner and the candesartan cilexetil is released rapidly (immediate release (IR)) and optionally the diuretic is released rapidly (immediate release (IR)) and the pharmaceutical dosage forms obtainable by these processes.

The calcium antagonist nifedipine is, as established active ingredient, successfully used in hypertension therapy and known from e.g. GB 1173862.

The angiotensin II antagonist candesartan, its prodrug candesartan cilexetil and its medicinal use as antihypertensive drug is known from EP 0 459 136.

Diuretics are medicaments used for eliminating water from the human or animal body. In some instances, elimination of salts, too, is increased. This results in a reduction of plasma volume and peripheral resistance. Diuretics are primarily employed for lowering blood pressure. There are various types of diuretics. Carboanhydrase inhibitors (acetazolamide): blockade of proton secretion and sodium bicarbonate re-absorption, mainly at the proximal tubulus. Nowadays use limited almost exclusively to ophthalmology for the treatment of glaucomas. Loop diuretics (furosemide, torasemide, bumetanide, etacrynic acid, piretanide): reversible inhibition of an Na/2Cl/K carrier system at the thick ascending limb of the loop of Henle. Potassium-sparing diuretics (amiloride, triamterene): blockade of the Na channels at the late distal tubulus and at the collecting tube, inhibition of Na re-absorption, as a consequence reduced K secretion. Aldosterone antagonists (spironolactone, potassium canrenoate, eplerenone): competitive binding at the aldosterone receptor, as a consequence inhibition of Na re-absorption and K secretion, used for ascites associated with cirrhosis of the liver and as additional therapeutic for chronic heart failure. Thiazide diuretics and other sulphonamide diuretics (hydrochlorothiazide (=HCTZ), chlorothiazide, chlorthalidone, xipamide, indapamide, mefruside): reversible inhibition of the Na—Cl cotransport at the early distal tubulus (luminal), inhibition of carboanhydrase, reduction of GFR, hydrochlorothiazide frequently employed in combination with antihypertensive agents. The addition of a diuretic such as, for example, HCTZ in monotherapy enhances the hypotensive action of the combination.

Combinations of a diuretic and angiotensin II antagonists are known to the person skilled in the art, for example from EP 1 306 088 B (candesartan and furosemide), but also the following fixed-dose combinations for treating high blood pressure such as, for example, Hyzaar® (=losartan potassium plus HCTZ) from Merck, Co-Diovan® (=valsartan plus HCTZ) from Novartis or Boehringer's Micardis Plus® (=telmisartan plus HCTZ).

In view of the biological properties of nifedipine and/or nisoldipine and the angiotensin II antagonists, it is crucial for both active ingredients to be absorbed from the low sections of the bowel without significant loss of bioavailability. This is the case with only about 30-50% of all active ingredients, and therefore appropriate selection of the combination active ingredients is crucially important for developing an IR/slow-release combination product.

It is advantageous especially for the long-term therapy or prophylaxis and secondary prophylaxis of cardiovascular disorders to have the active ingredients available in a form which, through a modified release of active ingredients, leads to a reduction in the peak-trough ratio and makes administration once a day possible.

In the development of formulations, account must also be taken of the physicochemical and biological properties of the active ingredients, for example the relatively low water solubility of nifedipine (approx. 9 mg/l) and the plasma half-life of about 2 hours. Accordingly, special pharmaceutical formulations with which nifedipine undergoes a modified release, taking account of its physicochemical and biological properties, are necessary for the desired administration once a day.

In the sense of the present invention the term release in the body in a controlled (modified) manner with respect to nifedipine has the meaning that 85% nifedipine (based on the declared amount of nifedipine) is released from the dosage form over a period of at least 4 and at most 24 hours, and less than 20% of the nifedipine within 4 hours, and from 43 to 80%, more preferably from 45 to 75%, in particular preferably from 50 to 70% of the nifedipine within 12 hours in an in-vitro release test carried out according to the USP release method using apparatus 2 (paddle) at 100 revolutions per minute in 900 mL of phosphate buffer pH 6.8 with addition of 1% sodium lauryl sulphate as the release medium at 37° C.

In the sense of the present invention the term release in the body is rapid (immediate release (IR)) with respect to candesartan cilexetil and/or a diuretic has the meaning that that at least 70%, preferably at least 80% of the candesartan cilexetil (based on the declared amount of the candesartan cilexetil) is dissolved within a period of 60 minutes in an in-vitro dissolution test carried out according to the USP dissolution method using apparatus 2 (paddle) at 75 revolutions per minute in 900 mL phosphate buffer pH 6.5 with the addition of 0.7% Tween 20 as the dissolution medium at 37° C.

In the sense of the present invention the term release in the body is rapid (immediate release (IR)) with respect to a diuretic has the meaning that that at least 70%, preferably at least 80% of the HTCZ (based on the declared amount of the HTCZ) is dissolved within a period of 60 minutes in an in-vitro dissolution test carried out according to the USP dissolution method using apparatus 2 (paddle) at 75 revolutions per minute in 900 mL phosphate buffer pH 6.5 with the addition of 0.7% Tween 20 as the dissolution medium at 37° C.

Combinations of an angiotensin II antagonist and, firstly, calcium channel blockers or, secondly, diuretics are known from WO 92/10097. Explicitly described are the combinations of eprosartan and nifedipine and eprosartan and hydrochlorothiazide. Specifically disclosed are fast-release hard gelatine capsules and tablets.

Combinations of candesartan cilexetil and hydrochlorothiazide are disclosed in EP 0 753 301B.

Dosage forms releasing the active compounds nifedipine or nisoldipine in combination with an angiotensin II antagonist in modified/delayed form and their preparation are described, for example, in WO 2007/003330. In these formulations, both nifedipine and the angiotensin II antagonist are released in delayed form.

WO2008/044862 discloses pharmaceutical dosage forms comprising an active ingredient combination of at least one calcium channel blocker and at least one angiotensin II antagonist characterized in that the calcium channel blocker is released after a certain lag time immediately whereas the angiotensin II antagonist is released immediately (chronotherapy). Explicitly disclosed are the combinations of losartan and amlodipine.

WO2010/060564 discloses pharmaceutical dosage forms comprising an active ingredient combination of nifedipine or nisoldipine and at least one angiotensin II antagonist and/or at least one diuretic, characterized in that nifedipine or nisoldipine is released in the body in a controlled (modified) manner and the angiotensin II antagonist and/or the diuretic is released rapidly (immediate release (IR)), and also processes for their preparation, to their use as medicaments and to their use for the prophylaxis, secondary prophylaxis or treatment of disorders.

Particularly suitable dosage forms with modified/delayed release of the active ingredient nifedipine are based on osmotic release systems. Preferably, in these osmotic release systems, bi-layer tablets are surrounded by a semipermeable membrane which has at least one orifice. The water-permeable membrane is impermeable for components of the core, but allows water to enter the system from outside by osmosis. The water which has penetrated in then releases, by the resulting osmotic pressure, the active ingredient in dissolved or suspended form from the orifice(s) in the membrane. The overall active ingredient release and the release rate can be controlled substantially via the thickness and porosity of the semipermeable membrane, the composition of the core and the number and size of the orifice(s). Advantages, formulation aspects, use forms and information on production processes are described inter alia in the following publications: U.S. Pat. Nos. 4,327,725, 4,765,989, US 20030161882, EP 1 024 793.

Coated osmotic release systems are likewise known. Thus, EP 0 339 811 describes an osmotic release system consisting of a cellulose acetate coat which comprises nifedipine and swelling agent in the core and is surrounded by a mantle coating of HPMC (hydroxypropylmethylcellulose) having a layer thickness of 0.0025 cm. U.S. Pat. No. 4,948,592, WO 93/03711 and WO 93/00071 describe osmotic release systems comprising a proportion of active ingredient in the core with a delayed release profile and a proportion of the same active ingredient in the mantle coating which can be released directly. Here, the mantle coatings comprise in each case only a small part of the total amount of active ingredient required for pharmaceutical activity. In such case, the pharmacopoeial requirements for content uniformity of dosage forms apply to the total amount of the active ingredient, to the sum of active ingredient in the core and in the mantle coating. Thus, the overall content variability of the active ingredient is somewhere between the typically low variability of tablets prepared by compression and the typically high variability of products prepared by film coating.

When rapid release of a second active ingredient is required, it is necessary to incorporate the entire amount of the second active ingredient into the outer mantle layer of the dosage form. In such cases, i.e. mantle coatings that contain the total amount of an active ingredient (active coatings), the pharmacopoeial requirements for content uniformity of dosage forms solely apply to the amount of the active ingredient in the mantle coating.

It is well known to those skilled in the art that pharmaceutical film coating processes typically result in a higher variability with regard to the mass of the film coating as compared to for example tableting processes with regard to the mass of the tablet cores. This is mainly due to the fact that film coating is a batch process. In a tableting process each single tablet is produced under the same conditions and thus, the variability of the tablet mass is typically low, i.e. relative standard deviations of the tablet mass are typically below 3%, in most cases even below 1.5%. In a pharmaceutical film coating process a complete batch of tablets is coated during a limited time and the film coating mass applied to each single tablets depends on how often and for how long time periods that specific tablets is exposed to the spraying zone. For that reason, the variability of the film coating mass is typically high, i.e. relative standard deviations of the film coating mass are generally above 5% and typically above 7.5% and often even above 15%. As film coatings are often used for cosmetic reasons only (e.g. colour and smooth surface), the high variability is not regarded as critical to the quality. This is also not the case when film coatings are used to protect the tablet from environment effects; in such cases the only requirement is that all tablets are sufficiently protected. In the case of modified release coatings, the film coating mass needs to be controlled in such a way that the variability of the drug release profile is acceptable. This can generally be achieved although the typical high variability of the film coating mass, as the sensitivity of the release profile variability to the film coating variability is less than proportional.

Furthermore, it is well known to those skilled in the art that pharmaceutical film coating processes typically exhibit a certain loss of coating suspension during spraying, i.e. a small but variable and hardly predictable portion of the sprayed coating suspension is deposited on the surface of the coater drum or removed with the exhaust air instead of being deposited on the tablets. In the cases of cosmetic and protective film coatings such losses are typically compensated by predefined overages of e.g. 5-15%. Also in the case of modified release coatings, overages are well established to compensate losses during spraying as the sensitivity of the release profile to the overall film coating mass is less than proportional.

However, in the case of active coatings (and especially if the active ingredient is solely present in the active coating), the inherent variability of the coating process and the poor predictability of spraying losses during manufacturing is in conflict with the pharmacopoeial requirements for content uniformity. Moreover, the pharmacopoeial requirements have become even stricter recently.

Challenges in developing fixed dose combinations using active coating technology are discussed by Desai et al., Pharmaceutical Development Fundamentals: Formulation design, challenges, and development considerations for fixed dose combination (FDC) of oral solid dosage forms, Pharmaceutical Development and Technology, 1-12 (2012). Chen et al., Modeling of pan coating process: Prediction of tablet content uniformity and determination of critical process parameters, Journal of Pharmaceutical Sciences 99, 3213-24 (2010) provide an overview on factors influencing the coating uniformity. Remarkably, according to these predictions acceptable coating uniformity is only achieved after undesirably long spraying times, such as e.g. up to 1200 min, i.e. 20 hours. Specific examples of active coating applications relating to selected active ingredients, specific coating polymers and specific tablet cores to be coated, are provided in US 2005/0214373 A1, US 2005/0266080 A1, and WO 2012/031124 A2. No general guidance how to optimize process conditions in order to improve active coating processes with regard to content uniformity and determination of coating endpoint are provided therein.

Furthermore, coating efficiency is regarded a specific challenge in active coating processes; e.g. Wang et al., An evaluation of process parameters to improve coating efficiency of an active tablet film-coating process, International Journal of Pharmaceutics 427, 163-169 (2012) describe means to optimize coating efficiency.

In the European Pharmacopoeia the requirements for the content uniformity of tablets used to be described in the general chapter 2.9.6 Uniformity of content of single-dose preparations. The acceptance criterion was that out of 10 tablets, all individual assays should be in the range of 85% to 115% of the average assay, or—as stage 2 testing—out of 30 tablets, all individual assays should be in the range of 75% to 125% of the average assay, and not more than 1 tablet should be outside the range of 85% to 115% of the average assay.

However, a new and stricter requirement has been introduced into the European Pharmacopoeia in the Supplement 5.2 as a new general chapter 2.9.40 Uniformity of dosage units. Therein, an acceptance value (AV) is defined as follows:

$$AV=|M-X|+ks$$

wherein X is the mean of the individual contents, M is the reference value, k is the acceptability constant and s is the sample standard deviation. The reference value is depending on the experimental results for X:

if X is between 98.5% and 101.5%, then M=X;
if X is below that range, then M=98.5%;
if X is above that range, then M=101.5%.

For example, if X is 97.5%, the term |M−X| results in 1%. Similarly, if X is 102.5%, the term |M−X| also results in 1%. For that reason, it is preferred that X is as close to 100% as possible, and it is particularly preferred that X is within the range of 98.5% to 101.5%.

The pharmacopoeial requirement is that AV should not exceed 15%. The test is first performed for n=10 tablets and the AV value is calculated using an acceptability constant of k=2.4. If this test fails, further 20 tablets can be investigated and the AV value for all n=30 tablets is calculated using an acceptability constant of k=2.4. In other words, in order to meet the new strict pharmacopoeial requirements for content uniformity, the mean value of the individual contents should be as close to the range of 98.5%-101.5% as possible. Simultaneously it is also necessary to control the standard deviation of the individual content below 7.5%, preferably significantly below 7.5%.

In addition to the AV requirement it is also required that all individual assays should be in the range of 75% to 125%.

Thus, there is a need to provide manufacturing processes for the dosage form comprising nifedipine and candesartan cilexetil and optionally a diuretic like HTCZ for all scales of pharmaceutical manufacturing that reliably and reproducibly lead to products fulfilling the pharmacopoeial requirements regarding content uniformity of the active ingredient solely present in an active coating. In other words, there is a need to provide active coating processes for all scales of pharmaceutical manufacturing that reliably and reproducibly control the mean of individual contents close to 100% and the respective standard deviation as low as possible, with an inter-tablet variability of the candesartan cilexetil content of less than 5%, preferably less than 4.8%, more preferably less than 4.5%.

It is well known to those skilled in the art, that as a means to improve the uniformity of active ingredient distribution, the active ingredient can be employed in a small particle size. For example, the active ingredient can be used in micronized form. However, in some cases micronization can negatively influence the stability of active ingredients. Without wishing to be limited to any specific theory, this may be due to the increase of reactive surface and/or partial amorphization during micronization, even if such amorphization occurs in a very low and hardly detectable extent.

In US 2007/0082055, it is disclosed that particle size reduction of candesartan cilexetil has an adverse effect on its chemical stability, namely micronization gives rise to the levels of the desethyl compound. In US 2007/0082055, it is further disclosed that the stability of candesartan cilexetil can be improved by a process comprising slurrying a sample of candesartan cilexetil of fine particle size in a suitable solvent for a suitable amount of time and recovering stable candesartan cilexetil of fine particle size.

WO 2008/045006 disclose the stabilization of candesartan cilexetil via the use of antioxidants. WO 2005/070398, WO 2005/084648, WO 2005/079751, and US 2010/0041644 disclose the stabilization of candesartan cilexetil by the use of several compounds, including esters, fatty substances, co-solvents and water-soluble polymers. WO 2005/084648 also mentions the potential use of polyvinyl alcohol.

Thus, there is a need to provide manufacturing processes for the dosage form comprising nifedipine and candesartan cilexetil and optionally a diuretic like HTCZ for all scales of pharmaceutical manufacturing that reliably and reproducibly lead to chemically stable products fulfilling the pharmacopoeial requirements regarding content uniformity of the active ingredient solely present in an active coating.

Terahertz pulsed imaging (TPI) is a recent non-destructive measurement technique that can be used to determine the coating thickness on pharmaceutical tablets. As an imaging technique it can spatially resolve the distribution of the coating layer over the entire surface of a tablet. The technique works by using short pulses of terahertz radiation (FWHM<1 ps), that are focused onto the surface of a tablet. Polymers are semitransparent to terahertz radiation and hence a part of the pulse can penetrate into the coating while the other part of the pulse is reflected to the detector. At every subsequent interface where a change in refractive index occurs, further parts of the pulse are reflected back and can be detected as additional reflection pulses (FIG. 2). Using the time-delay between the reflection pulses, the coating thickness of the material can be calculated. Detailed information about the measurement are dislosed in Zeitler et al., Terahertz pulsed spectroscopy and imaging in the pharmaceutical setting—a review. Journal of Pharmacy and Pharmacology 59, 209-223 (2007). Ho et al., Analysis of sustained-release tablet film coats using terahertz pulsed imaging, Journal of Controlled Release 119, 253-261 (2007) discloses a good agreement between coating thickness measurements obtained by TPI and microscopic reference data.

Ho et al., Monitoring the film coating unit operation and predicting drug dissolution using terahertz pulsed imaging, Journal of Pharmaceutical Sciences 98, 4866-4876 (2009) discloses the use of TPI technique to monitor the growth of the coating layer with process time during a coating run in off-line measurements.

May et al., Terahertz in-line sensor for direct coating thickness measurement of individual tablets during film coating in real-time, Journal of Pharmaceutical Sciences 100, 1535-1544 (2011) discloses the use of this technology to measure the coating thickness of individual tablets during a coating run (in-line). There are however no reports on the applicability of TPI measurements for thick coating layers (>200 μm) or active coating processes yet.

Both, NIR and Raman spectroscopy are known as a process analytical technology (PAT) tool for a variety of applications such as end point determination in blending, process control of granulation, drying and coating operations. De Beer et al., Near infrared and Raman spectroscopy for the in-process monitoring of pharmaceutical production processes, Int. J. Pharm. 417, 32-47 (2011) summarizes the state of the art in that respect.

NIR spectroscopy is being discussed as a powerful process analytical technology tool for more than a decade. Gendre et al., Development of a process analytical technology (PAT) for in-line monitoring of film thickness and mass of coating materials during a pan coating operation, Eur. J. Pharm. Sci. 43, 244-250 (2011) and Gendre et al., Real-time predictions of drug release and end point detection of a coating operation by in-line near infrared measurements, Int. J. Pharm. 421, 237-43 (2011) disclose the use of NIR spectroscopy to in-line monitor the film thickness and the corresponding effect on in vitro-release of modified release coatings. Active coatings are however not disclosed. Kim et al., Investigation of an active film coating to prepare new fixed-dose combination tablets for treatment of diabetes describe active film coatings containing glimepiride and the use of off-line NIR spectroscopy to monitor the coating process. Content uniformity data are however not reported while reported single values range from 93.1 to 108.1%. Accordingly, FIGS. 6 and 7 of Kim et al. also display significant variability.

The use of Raman spectroscopy as a potential process analytical technology tool has been proposed more recently. In comparison to NIR spectroscopy, Raman spectroscopy offers higher structural selectivity. Müller et al., Prediction of dissolution time and coating thickness of sustained release formulations using Raman spectroscopy and terahertz pulsed imaging, Eur J Pharm Biopharm. 80, 690-697 (2012) disclose the use of Raman spectroscopy to in-line monitor the film thickness and the corresponding effect on in vitro-release of modified release coatings. Müller et al., Feasibility of Raman spectroscopy as PAT tool in active coating. Drug. Dev. Ind. Pharm. 36, 234-243 (2010) and Müller et al., Validation of Raman spectroscopic procedures in agreement with ICH guideline Q2 with considering the transfer to real time monitoring of an active coating process, J. Pharm. Biomed. Anal. 53, 884-894 (2010) disclose the use of Raman spectroscopy to determine the amount of coatings containing the active pharmaceutical ingredient diprophylline. The active coatings were applied to uniform cores in these studies. Active coatings on bilayer tablets are however not disclosed. Obviously, bilayer tablet cores provide an inhomogeneous background for any spectroscopic measurements.

Thus, there is a need to provide a reliable method for endpoint control of the active coating step, especially onto bilayer tablet cores.

Thus, there is a need to provide a reliable method for endpoint control of the active coating step, especially onto bilayer tablet cores comprising Nifedipine.

Thus, there is a need to provide a reliable method for endpoint control of the active coating step for candesartan cilexetil, especially onto bilayer tablet cores comprising Nifedipine.

Thus, there is a need to provide a reliable method for endpoint control of the active coating step for candesartan cilexetil, especially onto osmotic release bilayer tablet cores comprising Nifedipine.

SUMMARY OF THE INVENTION

It is an object of the present invention to provide reliable and reproducible manufacturing processes for the preparation of pharmaceutical dosage forms comprising nifedipine and candesartan cilexetil characterized in that nifedipine is released in the body in a controlled (modified) manner and the candesartan cilexetil is released rapidly (immediate release (IR)).

It is another object of the present invention to provide reliable and reproducible manufacturing processes for the preparation of pharmaceutical dosage forms comprising nifedipine and candesartan cilexetil and optionally at least one diuretic characterized in that nifedipine is released in the body in a controlled (modified) manner and the candesartan cilexetil is released rapidly (immediate release (IR)) and that the diuretic is released rapidly (immediate release (IR)).

It is another object of the present invention to provide reliable and reproducible manufacturing processes for the preparation of pharmaceutical dosage forms in the form of a mantle-core tablet comprising nifedipine in an osmotic release bilayer tablet core of said mantle-core tablet and candesartan cilexetil in the mantle of said mantel-core tablet characterized in that nifedipine is released in the body in a controlled (modified) manner and the candesartan cilexetil is released rapidly (immediate release (IR)).

It is another object of the present invention to provide reliable and reproducible manufacturing processes for the preparation of pharmaceutical dosage forms comprising nifedipine and candesartan cilexetil characterized in that 85% nifedipine (based on the declared amount of nifedipine) is released from the dosage form over a period of at least 4 and at most 24 hours, and less than 20% of the nifedipine within 4 hours, and from 43 to 80%, more preferably from 45 to 75%, in particular preferably from 50 to 70% of the nifedipine within 12 hours in an in-vitro release test carried out according to the USP release method using apparatus 2 (paddle) at 100 revolutions per minute in 900 mL of phosphate buffer pH 6.8 with addition of 1% sodium lauryl sulphate as the release medium at 37° C., and that at least 70%, preferably at least 80% of the candesartan cilexetil (based on the declared amount of the candesartan cilexetil) is dissolved within a period of 60 minutes in an in-vitro dissolution test carried out according to the USP dissolution method using apparatus 2 (paddle) at 75 revolutions per minute in 900 mL phosphate buffer pH 6.5 with the addition of 0.7% Tween 20 as the dissolution medium at 37° C.

It is another object of the present invention to provide pharmaceutical dosage forms comprising nifedipine and candesartan cilexetil obtainable by reliable and reproducible manufacturing processes characterized in that nifedipine is released in the body in a controlled (modified) manner and the candesartan cilexetil is released rapidly (immediate release (IR)).

It is another object of the present invention to provide a pharmaceutical dosage form comprising nifedipine and candesartan cilexetil and a diuretic which is preferably hydrochlorothiazide, chlorthalidone, mefruside, piretanide or indapamide obtainable by reliable and reproducible manufacturing processes characterized in that nifedipine is released in the body in a controlled (modified) manner and the candesartan cilexetil and the diuretic are released rapidly (immediate release (IR)).

It is another object of the present invention to provide a pharmaceutical dosage form comprising nifedipine and candesartan cilexetil and a diuretic which is preferably hydrochlorothiazide or chlorthalidone obtainable by reliable and reproducible manufacturing processes characterized in that nifedipine is released in the body in a controlled (modified) manner and the candesartan cilexetil and the diuretic are released rapidly (immediate release (IR)).

It is another object of the present invention to provide pharmaceutical dosage forms comprising nifedipine and candesartan cilexetil with a low inter- and/or intra tablet variability obtainable by reliable and reproducible manufacturing processes characterized in that nifedipine is released in the body in a controlled (modified) manner and the candesartan cilexetil is released rapidly (immediate release (IR)).

It is another object of the present invention to provide pharmaceutical dosage forms comprising nifedipine and candesartan cilexetil with an inter-tablet variability of the candesartan cilexetil content of less than 5%, preferably less than 4.8%, more preferably less than 4.5% obtainable by reliable and reproducible manufacturing processes characterized in that nifedipine is released in the body in a controlled (modified) manner and the candesartan cilexetil is released rapidly (immediate release (IR)).

It is another object of the present invention to provide pharmaceutical dosage forms in the form of mantle-core tablets comprising nifedipine in an osmotic release bilayer tablet core of said mantle-core tablet and candesartan cilexetil in the mantle of said mantel-core tablet by reliable and reproducible manufacturing processes for the preparation of pharmaceutical dosage forms, characterized in that nifedipine is released in the body in a controlled (modified) manner and the candesartan cilexetil is released rapidly (immediate release (IR)).

It is another object of the present invention to provide pharmaceutical dosage forms comprising nifedipine and candesartan cilexetil obtainable by reliable and reproducible manufacturing processes, characterized in that 85% nifedipine (based on the declared amount of nifedipine) is released from the dosage form over a period of at least 4 and at most 24 hours, and less than 20% of the nifedipine within 4 hours, and from 43 to 80%, more preferably from 45 to 75%, in particular preferably from 50 to 70% of the nifedipine within 12 hours in an in-vitro release test carried out according to the USP release method using apparatus 2 (paddle) at 100 revolutions per minute in 900 mL of phosphate buffer pH 6.8 with addition of 1% sodium lauryl sulphate as the release medium at 37° C., and that at least 70%, preferably at least 80% of the candesartan cilexetil (based on the declared amount of the candesartan cilexetil) is dissolved within a period of 60 minutes in an in-vitro dissolution test carried out according to the USP dissolution method using apparatus 2 (paddle) at 75 revolutions per minute in 900 mL phosphate buffer pH 6.5 with the addition of 0.7% Tween 20 as the dissolution medium at 37° C.

It is another object of the present invention to provide pharmaceutical dosage forms comprising nifedipine and candesartan cilexetil obtainable by reliable and reproducible manufacturing processes, characterized in that it contains nifedipine in a minimum dose of 5 mg and a maximum dose of 90 mg.

It is another object of the present invention to provide pharmaceutical dosage forms comprising nifedipine and candesartan cilexetil obtainable by reliable and reproducible manufacturing processes, characterized in that it contains nifedipine in a minimum dose of 10 mg and a maximum dose of 60 mg.

It is another object of the present invention to provide pharmaceutical dosage forms comprising nifedipine and candesartan cilexetil obtainable by reliable and reproducible manufacturing processes, characterized in that it contains nifedipine in a dose of 20 mg, 30 mg or 60 mg.

It is another object of the present invention to provide pharmaceutical dosage forms comprising nifedipine and candesartan cilexetil obtainable by reliable and reproducible manufacturing processes, characterized in that candesartan cilexetil is employed in a dose of 2-32 mg.

It is another object of the present invention to provide pharmaceutical dosage forms comprising nifedipine and candesartan cilexetil obtainable by reliable and reproducible manufacturing processes, characterized in that candesartan cilexetil is employed in a dose of 8-32 mg.

It is another object of the present invention to provide pharmaceutical dosage forms comprising nifedipine and candesartan cilexetil obtainable by reliable and reproducible manufacturing processes, characterized in that candesartan cilexetil is employed in a dose of 4 mg, 8 mg, 16 mg or 32 mg.

Surprisingly, with the present invention it is possible to provide reliable and reproducible manufacturing processes in all scales of pharmaceutical manufacturing for the preparation of pharmaceutical dosage forms comprising nifedipine and candesartan cilexetil and optionally a diuretic like HTCZ characterized in that nifedipine is released in the body in a controlled (modified) manner and the candesartan cilexetil is released rapidly (immediate release (IR)) and the diuretic is released rapidly (immediate release (IR)) and the products obtainable by this process.

Furthermore, the present invention surprisingly provides control of the manufacturing process in a way that it reliably and reproducibly results in a pharmaceutical dosage form containing the desired amount of candesartan cilexetil in the active coating layer. Similarly, the present invention surprisingly enables the control of the manufacturing process in all scales of pharmaceutical manufacturing in a way that it reliably and reproducibly results in a pharmaceutical dosage form containing candesartan cilexetil in the active coating layer with a low inter-tablet variability of the candesartan cilexetil content, e.g. of less than 5%, preferably less than 4.8%, more preferably less than 4.5%. Thus, by controlling the mean content close to the target content and/or by keeping the inter-tablet variability low, the present invention provides a manufacturing process that reliably and reproducibly leads to a pharmaceutical dosage form compliant to pharmacopoeial requirements.

Furthermore, the present invention surprisingly provides control of the manufacturing process in all scales of pharmaceutical manufacturing in a way that it reliably and reproducibly results in high process yields. Thus, the present invention provides the opportunity to reduce production losses, especially with regard to the active ingredient containing active coating suspension.

Furthermore, the present invention surprisingly provides control of the manufacturing process in all scales of pharmaceutical manufacturing in a way that it reliably and reproducibly results in a pharmaceutical dosage form containing candesartan cilexetil in the active coating layer with a low intra-tablet variability of the candesartan cilexetil content, e.g. of less than 5%, preferably less than 4.8%, more preferably less than 4.5%.

Furthermore, the present invention surprisingly results in stable pharmaceutical dosage forms even if micronized candesartan cilexetil is used for the manufacturing.

Figure 1:
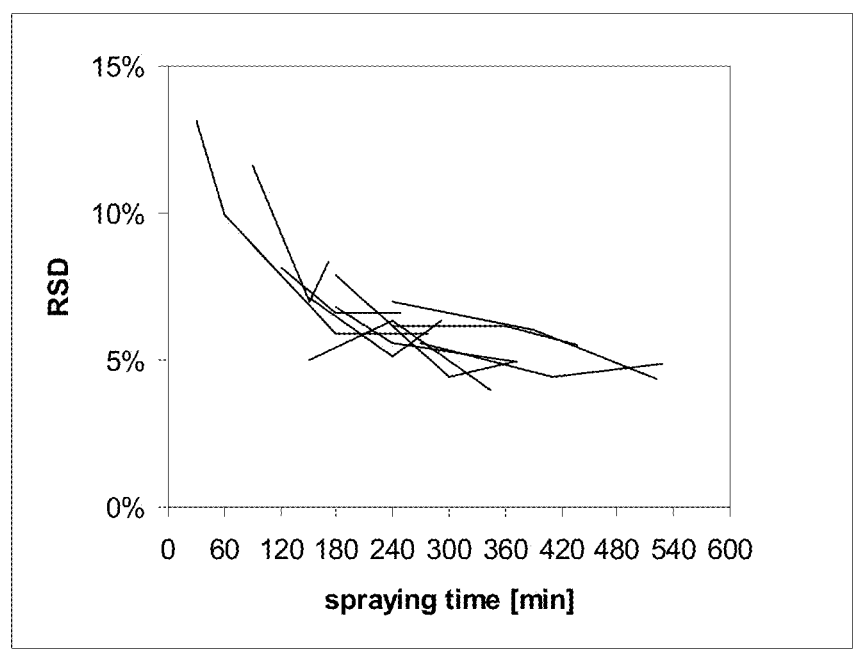
FIG. 1 is a plot of relative standard deviation (RSD) of candesartan cilexetil content vs spraying time from tablet cores coated under different conditions, as set forth in Example 7, and from in-process control samples.

EXAMPLES (1) Thus, the invention provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the spraying step of the candesartan cilexetil active coating process is performed at a drum load of 60 to 90%, preferably 60 to 80% of the nominal drum capacity.

(2) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the peripheral speed of the coating drum exceeds 0.3 m/s, preferably peripheral speed of the coating drum exceeds 0.4 m/s, more preferably peripheral speed of the coating drum exceeds 0.6 m/s.

(3) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the spraying process is performed substantially continuously over at least a scale and equipment specific minimum spraying time and optionally over the two-fold, preferably the 1.5-fold, preferably the 1.4-fold, more preferably the 1.2-fold, most preferably the 1.1-fold of that time as a maximum spraying time.

(4) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the spraying process is performed substantially continuously over at least 3 hours, preferably over at least 4 hours, most preferably over at least 6 hours and optionally over the two-fold, preferably the 1.5-fold, preferably the 1.4-fold, more preferably the 1.2-fold, most preferably the 1.1-fold of any of those times as a maximum spraying time.

(5) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the spraying process is performed using at least 4 spray nozzles.

(6) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the spraying step of the candesartan cilexetil active coating process is performed at a drum load of 60 to 90%, preferably 60 to 80% of the nominal drum capacity and that the peripheral speed of the coating drum exceeds 0.3 m/s, preferably peripheral speed of the coating drum exceeds 0.4 m/s, more preferably peripheral speed of the coating drum exceeds 0.6 m/s.

(7) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the spraying step of the candesartan cilexetil active coating process is performed at a drum load of 60 to 90%, preferably 60 to 80% of the nominal drum capacity and that the spraying process is performed substantially continuously over at least a scale and equipment specific minimum spraying time and optionally over the two-fold, preferably the 1.5-fold, preferably the 1.4-fold, more preferably the 1.2-fold, most preferably the 1.1-fold of that time as a maximum spraying time.

(8) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the spraying step of the candesartan cilexetil active coating process is performed at a drum load of 60 to 90%, preferably 60 to 80% of the nominal drum capacity and that the spraying process is performed substantially continuously over at least 3 hours, preferably over at least 4 hours, most preferably over at least 6 hours and optionally over the two-fold, preferably the 1.5-fold, preferably the 1.4-fold, more preferably the 1.2-fold, most preferably the 1.1-fold of any of those times as a maximum spraying time.

(9) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the spraying step of the candesartan cilexetil active coating process is performed at a drum load of 60 to 90%, preferably 60 to 80% of the nominal drum capacity and that the spraying process is performed using at least 4 spray nozzles.

(10) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the peripheral speed of the coating drum exceeds 0.3 m/s preferably peripheral speed of the coating drum exceeds 0.4 m/s, more preferably peripheral speed of the coating drum exceeds 0.6 m/s and that the spraying process is performed substantially continuously over at least a scale and equipment specific minimum spraying time and optionally over the two-fold, preferably the 1.5-fold, preferably the 1.4-fold, more preferably the 1.2-fold, most preferably the 1.1-fold of that time as a maximum spraying time.

(11) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the peripheral speed of the coating drum exceeds 0.3 m/s preferably peripheral speed of the coating drum exceeds 0.4 m/s, more preferably peripheral speed of the coating drum exceeds 0.6 m/s and that the spraying process is performed substantially continuously over at least 3 hours, preferably over at least 4 hours, most preferably over at least 6 hours and optionally over the two-fold, preferably the 1.5-fold, preferably the 1.4-fold, more preferably the 1.2-fold, most preferably the 1.1-fold of any of those times as a maximum spraying time.

(12) The invention further provides a process for the manufacture of a pharmaceutical dosage form comprising nifedipine in the core and candesartan cilexetil in the active coating layer with an inter-tablet variability of the candes artan cilexetil content of less than 5%, preferably less than 4.8%, more preferably less than 4.5%, characterized in that the peripheral speed of the coating drum exceeds 0.3 m/s preferably peripheral speed of the coating drum exceeds 0.4 m/s, more preferably peripheral speed of the coating drum exceeds 0.6 m/s and that the spraying process is performed using at least 4 spray nozzles.

(13) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the spraying process is performed substantially continuously over at least a scale and equipment specific minimum spraying time and optionally over the two-fold, the 1.5-fold, preferably the 1.4-fold, more preferably the 1.2-fold, most preferably the 1.1-fold of that time as a maximum spraying time and that the spraying process is performed using at least 4 spray nozzles.

(14) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the spraying process is performed substantially continuously over at least 3 hours, preferably over at least 4 hours, most preferably over at least 6 hours and optionally over the two-fold, preferably the 1.5-fold, preferably the 1.4-fold, more preferably the 1.2-fold, most preferably the 1.1-fold of any of those times as a maximum spraying time and that the spraying process is performed using at least 4 spray nozzles.

(15) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the spraying step of the candesartan cilexetil active coating process is performed at a drum load of 60 to 90%, preferably 60 to 80% of the nominal drum capacity and that the peripheral speed of the coating drum exceeds 0.3 m/s, preferably peripheral speed of the coating drum exceeds 0.4 m/s, more preferably peripheral speed of the coating drum exceeds 0.6 m/s and that the spraying process is performed substantially continuously over at least a scale and equipment specific minimum spraying time and optionally over the two-fold, preferably the 1.5-fold, preferably the 1.4-fold, more preferably the 1.2-fold, most preferably the 1.1-fold of that time as a maximum spraying time.

(16) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the spraying step of the candesartan cilexetil active coating process is performed at a drum load of 60 to 90%, preferably 60 to 80% of the nominal drum capacity and that the peripheral speed of the coating drum exceeds 0.3 m/s, preferably peripheral speed of the coating drum exceeds 0.4 m/s, more preferably peripheral speed of the coating drum exceeds 0.6 m/s and that the spraying process is performed substantially continuously over at least 3 hours, preferably over at least 4 hours, most preferably over at least 6 hours and optionally over the two-fold, preferably the 1.5-fold, preferably the 1.4-fold, more preferably the 1.2-fold, most preferably the 1.1-fold of any of those times as a maximum spraying time.

(17) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the spraying step of the candesartan cilexetil active coating process is performed at a drum load of 60 to 90%, preferably 60 to 80% of the nominal drum capacity and that the peripheral speed of the coating drum exceeds 0.3 m/s, preferably peripheral speed of the coating drum exceeds 0.4 m/s, more preferably peripheral speed of the coating drum exceeds 0.6 m/s and that the spraying process is performed using at least 4 spray nozzles.

(18) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the spraying step of the candesartan cilexetil active coating process is performed at a drum load of 60 to 90%, preferably 60 to 80% of the nominal drum capacity and that the spraying process is performed substantially continuously over at least a scale and equipment specific minimum spraying time and optionally over two-fold, preferably the 1.5-fold, preferably the 1.4-fold, more preferably the 1.2-fold, most preferably the 1.1-fold of that time as a maximum spraying time and that the spraying process is performed using at least 4 spray nozzles.

(19) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the spraying step of the candesartan cilexetil active coating process is performed at a drum load of 60 to 90%, preferably 60 to 80% of the nominal drum capacity and that the spraying process is performed substantially continuously over at least 3 hours, preferably over at least 4 hours, most preferably over at least 6 hours and optionally over the two-fold, preferably the 1.5-fold, preferably the 1.4-fold, more preferably the 1.2-fold, most preferably the 1.1-fold of any of those times as a maximum spraying time and that the spraying process is performed using at least 4 spray nozzles.

(20) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the peripheral speed of the coating drum exceeds 0.3 m/s, preferably peripheral speed of the coating drum exceeds 0.4 m/s, more preferably peripheral speed of the coating drum exceeds 0.6 m/s and that the spraying process is performed substantially continuously over at least a scale and equipment specific minimum spraying time and optionally over the two-fold, preferably the 1.5-fold, preferably the 1.4-fold, more preferably the 1.2-fold, most preferably the 1.1-fold of that time as a maximum spraying time and that the spraying process is performed using at least 4 spray nozzles.

(21) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the peripheral speed of the coating drum exceeds 0.3 m/s, preferably peripheral speed of the coating drum exceeds 0.4 m/s, more preferably peripheral speed of the coating drum exceeds 0.6 m/s and that the spraying process is performed substantially continuously over at least 3 hours, preferably over at least 4 hours, most preferably over at least 6 hours and optionally over the two-fold, preferably the 1.5-fold, preferably the 1.4-fold, more preferably the 1.2-fold, most preferably the 1.1-fold of any of those times as a maximum spraying time and that the spraying process is performed using at least 4 spray nozzles.

(22) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the spraying step of the candesartan cilexetil active coating process is performed at a drum load of 60 to 90%, preferably 60 to 80% of the nominal drum capacity and that the peripheral speed of the coating drum exceeds 0.3 m/s, preferably peripheral speed of the coating drum exceeds 0.4 m/s, more preferably peripheral speed of the coating drum exceeds 0.6 m/s and that the spraying process is performed substantially continuously over at least a scale and equipment specific minimum spraying time and optionally over the two-fold, preferably the 1.5-fold, preferably the 1.4-fold, more preferably the 1.2-fold, most preferably the 1.1-fold of that time as a maximum spraying time and that the spraying process is performed using at least 4 spray nozzles.

(23) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, characterized in that the spraying step of the candesartan cilexetil active coating process is performed at a drum load of 60 to 90%, preferably 60 to 80% of the nominal drum capacity and that the peripheral speed of the coating drum exceeds 0.3 m/s, preferably peripheral speed of the coating drum exceeds 0.4 m/s, more preferably peripheral speed of the coating drum exceeds 0.6 m/s and that the spraying process is performed substantially continuously over at least 3 hours, preferably over at least 4 hours, most preferably over at least 6 hours and optionally over the two-fold, preferably the 1.5-fold, preferably the 1.4-fold, more preferably the 1.2-fold, most preferably the 1.1-fold of any of those times as a maximum spraying time and that the spraying process is performed using at least 4 spray nozzles.

(24) The invention further provides a process for the manufacture of a pharmaceutical dosage form comprising nifedipine in the core and candesartan cilexetil in the active coating layer with mean candesartan cilexetil content of 95-105%, preferably 98.5-101.5% characterized in that the candesartan cilexetil active coating process is performed until the desired amount of candesartan cilexetil has been applied to the tablets as determined by in-line NIR or Raman spectroscopy, preferably by in-line Raman spectroscopy.

(25) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-

101.5% characterized in that the spraying step of the candesartan cilexetil active coating process is performed at a drum load of 60 to 90%, preferably 60 to 80% of the nominal drum drum capacity and that the candesartan cilexetil active coating process is performed until the desired amount of candesartan cilexetil has been applied to the tablets as determined by in-line NIR or Raman spectroscopy, preferably by in-line Raman spectroscopy.

(26) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the peripheral speed of the coating drum exceeds 0.3 m/s, preferably peripheral speed of the coating drum exceeds 0.4 m/s, more preferably peripheral speed of the coating drum exceeds 0.6 m/s and that the candesartan cilexetil active coating process is performed until the desired amount of candesartan cilexetil has been applied to the tablets as determined by in-line NIR or Raman spectroscopy, preferably by in-line Raman spectroscopy.

(27) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the spraying process is performed substantially continuously over at least a scale and equipment specific minimum spraying time and optionally over the two-fold, preferably the 1.5-fold, preferably the 1.4-fold, more preferably the 1.2-fold, most preferably the 1.1-fold of that time as a maximum spraying time and that the candesartan cilexetil active coating process is performed until the desired amount of candesartan cilexetil has been applied to the tablets as determined by in-line NIR or Raman spectroscopy, preferably by in-line Raman spectroscopy.

(28) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the spraying process is performed substantially continuously over at least 3 hours, preferably over at least 4 hours, most preferably over at least 6 hours and optionally over the two-fold, preferably the 1.5-fold, preferably the 1.4-fold, more preferably the 1.2-fold, most preferably the 1.1-fold of any of those times as a maximum spraying time and that the candesartan cilexetil active coating process is performed until the desired amount of candesartan cilexetil has been applied to the tablets as determined by in-line NIR or Raman spectroscopy, preferably by in-line Raman spectroscopy.

(29) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the spraying process is performed using at least 4 spray nozzles and that the candesartan cilexetil active coating process is performed until the desired amount of candesartan cilexetil has been applied to the tablets as determined by in-line NIR or Raman spectroscopy, preferably by in-line Raman spectroscopy.

(30) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the spraying step of the candesartan cilexetil active coating process is performed at a drum load of 60 to 90%, preferably 60 to 80% of the nominal drum capacity and that the peripheral speed of the coating drum exceeds 0.3 m/s, preferably peripheral speed of the coating drum exceeds 0.4 m/s, more preferably peripheral speed of the coating drum exceeds 0.6 m/s and that the candesartan cilexetil active coating process is performed until the desired amount of candesartan cilexetil has been applied to the tablets as determined by in-line NIR or Raman spectroscopy, preferably by in-line Raman spectroscopy.

(31) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the spraying step of the candesartan cilexetil active coating process is performed at a drum load of 60 to 90%, preferably 60 to 80% of the nominal drum capacity and that the spraying process is performed substantially continuously over at least a scale and equipment specific minimum spraying time and optionally over the two-fold, preferably the 1.5-fold, preferably the 1.4-fold, more preferably the 1.2-fold, most preferably the 1.1-fold of that time as a maximum spraying time and that the candesartan cilexetil active coating process is performed until the desired amount of candesartan cilexetil has been applied to the tablets as determined by in-line NIR or Raman spectroscopy, preferably by in-line Raman spectroscopy.

(32) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the spraying step of the candesartan cilexetil active coating process is performed at a drum load of 60 to 90%, preferably 60 to 80% of the nominal drum capacity and that the spraying process is performed substantially continuously over at least 3 hours, preferably over at least 4 hours, most preferably over at least 6 hours and optionally over the two-fold, preferably the 1.5-fold, preferably the 1.4-fold, more preferably the 1.2-fold, most preferably the 1.1-fold of any of those times as a maximum spraying time and that the candesartan cilexetil active coating process is performed until the desired amount of candesartan cilexetil has been applied to the tablets as determined by in-line NIR or Raman spectroscopy, preferably by in-line Raman spectroscopy.

(33) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the spraying step of the candesartan cilexetil active coating process is performed at a drum load of 60 to 90%, preferably 60 to 80% of the nominal drum capacity and that the spraying process is performed using at least 4 spray nozzles and that the candesartan cilexetil active coating process is performed until the desired amount of candesartan cilexetil has been applied to the tablets as determined by in-line NIR or Raman spectroscopy, preferably by in-line Raman spectroscopy.

(34) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the peripheral speed of the coating drum exceeds 0.3 m/s, preferably peripheral speed of the coating drum exceeds 0.4 m/s, more preferably peripheral speed of the coating drum exceeds 0.6 m/s and that the spraying process is performed substantially continuously over at least a scale and equipment specific minimum spraying time and optionally over the two-fold, preferably the 1.5-fold, preferably the 1.4-fold, more preferably the 1.2-fold, most preferably the 1.1-fold of that time as a maximum spraying time and that the candesartan cilexetil active coating process is performed until the desired amount of candesartan cilexetil has been applied to the tablets as determined by in-line NIR or Raman spectroscopy, preferably by in-line Raman spectroscopy.

(35) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the peripheral speed of the coating drum exceeds 0.3 m/s and that the spraying process is performed substantially continuously over at least 3 hours, preferably over at least 4 hours, most preferably over at least 6 hours and optionally over the two-fold, preferably the 1.5-fold, preferably the 1.4-fold, more preferably the 1.2-fold, most preferably the 1.1-fold of any of those times as a maximum spraying time and that the candesartan cilexetil active coating process is performed until the desired amount of candesartan cilexetil has been applied to the tablets as determined by in-line NIR or Raman spectroscopy, preferably by in-line Raman spectroscopy.

(36) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the peripheral speed of the coating drum exceeds 0.3 m/s, preferably peripheral speed of the coating drum exceeds 0.4 m/s, more preferably peripheral speed of the coating drum exceeds 0.6 m/s and that the spraying process is performed using at least 4 spray nozzles and that the candesartan cilexetil active coating process is performed until the desired amount of candesartan cilexetil has been applied to the tablets as determined by in-line NIR or Raman spectroscopy, preferably by in-line Raman spectroscopy.

(37) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the spraying process is performed substantially continuously over at least a scale and equipment specific minimum spraying time and optionally over the two-fold, preferably the 1.5-fold, preferably the 1.4-fold, more preferably the 1.2-fold, most preferably the 1.1-fold of that time as a maximum spraying time and that the spraying process is performed using at least 4 spray nozzles and that the candesartan cilexetil active coating process is performed until the desired amount of candesartan cilexetil has been applied to the tablets as determined by in-line NIR or Raman spectroscopy, preferably by in-line Raman spectroscopy.

(38) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the spraying process is performed substantially continuously over at least 3 hours, preferably over at least 4 hours, most preferably over at least 6 hours and optionally over the two-fold, preferably the 1.5-fold, preferably the 1.4-fold, more preferably the 1.2-fold, most preferably the 1.1-fold of any of those times as a maximum spraying time and that the spraying process is performed using at least 4 spray nozzles and that the candesartan cilexetil active coating process is performed until the desired amount of candesartan cilexetil has been applied to the tablets as determined by in-line NIR or Raman spectroscopy, preferably by in-line Raman spectroscopy.

(39) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the spraying step of the candesartan cilexetil active coating process is performed at a drum load of 60 to 90%, preferably 60 to 80% of the nominal drum capacity and that the peripheral speed of the coating drum exceeds 0.3 m/s, preferably peripheral speed of the coating drum exceeds 0.4 m/s, more preferably peripheral speed of the coating drum exceeds 0.6 m/s and that the spraying process is performed substantially continuously over at least a scale and equipment specific minimum spraying time and optionally over the two-fold, preferably the 1.5-fold, preferably the 1.4-fold, more preferably the 1.2-fold, most preferably the 1.1-fold of that time as a maximum spraying time and that the candesartan cilexetil active coating process is performed until the desired amount of candesartan cilexetil has been applied to the tablets as determined by in-line NIR or Raman spectroscopy, preferably by in-line Raman spectroscopy.

(40) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the spraying step of the candesartan cilexetil active coating process is performed at a drum load of 60 to 90%, preferably 60 to 80% of the nominal drum capacity and that the peripheral speed of the coating drum exceeds 0.3 m/s, preferably peripheral speed of the coating drum exceeds 0.4 m/s, more preferably peripheral speed of the coating drum exceeds 0.6 m/s and that the spraying process is performed substantially continuously over at least 3 hours, preferably over at least 4 hours, most preferably over at least 6 hours and optionally over the two-fold, preferably the 1.5-fold, preferably the 1.4-fold, more preferably the 1.2-fold, most preferably the 1.1-fold of any of those times as a maximum spraying time and that the candesartan cilexetil active coating process is performed until the desired amount of candesartan cilexetil has been applied to the tablets as determined by in-line NIR or Raman spectroscopy, preferably by in-line Raman spectroscopy.

(41) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the spraying step of the candesartan cilexetil active coating process is performed at a drum load of 60 to 90%, preferably 60 to 80% of the nominal drum capacity and that the peripheral speed of the coating drum exceeds 0.3 m/s, preferably peripheral speed of the coating drum exceeds 0.4 m/s, more preferably peripheral speed of the coating drum exceeds 0.6 m/s and that the spraying process is performed using at least 4 spray nozzles and that the candesartan cilexetil active coating process is performed until the desired amount of candesartan cilexetil has been applied to the tablets as determined by in-line NIR or Raman spectroscopy, preferably by in-line Raman spectroscopy.

(42) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the spraying step of the candesartan cilexetil active coating process is performed at a drum load of 60 to 90%, preferably 60 to 80% of the nominal drum capacity and that the spraying process is performed substantially continuously over at least a scale and equipment specific minimum spraying time and optionally over the two-fold, preferably the 1.5-fold, preferably the 1.4-fold, more preferably the 1.2-fold, most preferably the 1.1-fold of that time as a maximum spraying time and that the spraying process is performed using at least 4 spray nozzles and that the candesartan cilexetil active coating process is performed until the desired amount of candesartan cilexetil has been applied to the tablets as determined by in-line NIR or Raman spectroscopy, preferably by in-line Raman spectroscopy.

(43) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the spraying step of the candesartan cilexetil active coating process is performed at a drum load of 60 to 90%, preferably 60 to 80% of the nominal drum capacity and that the spraying process is performed substantially continuously over at least 3 hours, preferably over at least 4 hours, most preferably over at least 6 hours and optionally over the two-fold, preferably the 1.5-fold, preferably the 1.4-fold, more preferably the 1.2-fold, most preferably the 1.1-fold of any of those times as a maximum spraying time and that the spraying process is performed using at least 4 spray nozzles and that the candesartan cilexetil active coating process is performed until the desired amount of candesartan cilexetil has been applied to the tablets as determined by in-line NIR or Raman spectroscopy, preferably by in-line Raman spectroscopy.

(44) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the peripheral speed of the coating drum exceeds 0.3 m/s, preferably peripheral speed of the coating drum exceeds 0.4 m/s, more preferably peripheral speed of the coating drum exceeds 0.6 m/s and that the spraying process is performed substantially continuously over at least a scale and equipment specific minimum spraying time and optionally over the two-fold, preferably the 1.5-fold, preferably the 1.4-fold, more preferably the 1.2-fold, most preferably the 1.1-fold of that time as a maximum spraying time and that the spraying process is performed using at least 4 spray nozzles and that the candesartan cilexetil active coating process is performed until the desired amount of candesartan cilexetil has been applied to the tablets as determined by in-line NIR or Raman spectroscopy, preferably by in-line Raman spectroscopy.

(45) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the peripheral speed of the coating drum exceeds 0.3 m/s, preferably peripheral speed of the coating drum exceeds 0.4 m/s, more preferably peripheral speed of the coating drum exceeds 0.6 m/s and that the spraying process is performed substantially continuously over at least 3 hours, preferably over at least 4 hours, most preferably over at least 6 hours and optionally over the two-fold, preferably the 1.5-fold, preferably the 1.4-fold, more preferably the 1.2-fold, most preferably the 1.1-fold of any of those times as a maximum spraying time and that the spraying process is performed using at least 4 spray nozzles and that the candesartan cilexetil active coating process is performed until the desired amount of candesartan cilexetil has been applied to the tablets as determined by in-line NIR or Raman spectroscopy, preferably by in-line Raman spectroscopy.

(46) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the spraying step of the candesartan cilexetil active coating process is performed at a drum load of 60 to 90%, preferably 60 to 80% of the nominal drum capacity and that the peripheral speed of the coating drum exceeds 0.3 m/s, preferably peripheral speed of the coating drum exceeds 0.4 m/s, more preferably peripheral speed of the coating drum exceeds 0.6 m/s and that the spraying process is performed substantially continuously over at least a scale and equipment specific minimum spraying time and optionally over the two-fold, preferably the 1.5-fold, preferably the 1.4-fold, more preferably the 1.2-fold, most preferably the 1.1-fold of that time as a maximum spraying time and that the spraying process is performed using at least 4 spray nozzles and that the candesartan cilexetil active coating process is performed until the desired amount of candesartan cilexetil has been applied to the tablets as determined by in-line NIR or Raman spectroscopy, preferably by in-line Raman spectroscopy.

(47) The invention further provides a process for the manufacture of a pharmaceutical dosage form comprising nifedipine in the core and candesartan cilexetil in the active coating layer with an inter-tablet variability of the candesartan cilexetil content of less than 5%, preferably less than 4.8%, more preferably less than 4.5%, and with mean candesartan cilexetil content of 95-105%, preferably 98.5-101.5% characterized in that the spraying step of the candesartan cilexetil active coating process is performed at a drum load of 60 to 90%, preferably 60 to 80% of the nominal drum capacity and that the peripheral speed of the coating drum exceeds 0.3 m/s, preferably peripheral speed of the coating drum exceeds 0.4 m/s, more preferably peripheral speed of the coating drum exceeds 0.6 m/s and that the spraying process is performed substantially continuously over at least 3 hours, preferably over at least 4 hours, most preferably over at least 6 hours and optionally over the two-fold, preferably the 1.5-fold, preferably the 1.4-fold, more preferably the 1.2-fold, most preferably the 1.1-fold of any of those times as a maximum spraying time and that the spraying process is performed using at least 4 spray nozzles and that the candesartan cilexetil active coating process is performed until the desired amount of candesartan cilexetil has been applied to the tablets as determined by in-line NIR or Raman spectroscopy, preferably by in-line Raman spectroscopy.

(48) The invention further provides a process for the manufacture of a pharmaceutical dosage form according to any of claims/embodiments 24 to 47 comprising nifedipine in the core and candesartan cilexetil in the active coating layer characterized in that the candesartan cilexetil active coating process is performed until the desired amount of candesartan cilexetil has been applied to the tablets as determined by Raman spectroscopy, preferably by in-line Raman spectroscopy, preferably determined by in-line Raman spectroscopy using a PhAT probe and SNV preprocessed spectra in the spectral region from 1540 $cm^{-1}$ to 1750 $cm^{-1}$.

(49) The invention further provides a process for the manufacture of a pharmaceutical dosage form according to any of claims/embodiments (1) to (48) comprising nifedipine in the core and candesartan cilexetil in the active coating layer with an intra-tablet variability of the film thickness of the active film coating of less than 5%.

(50) The invention further provides a process for the manufacture of a pharmaceutical dosage form according to any of claims/embodiments (1) to (49) comprising nifedipine in the core and candesartan cilexetil in the active coating layer with an intra-tablet variability of the film thickness of the candesartan cilexetil film coating of less than 5%.

(51) The invention further provides a method to determine the scale and equipment specific minimum spraying time for the process for the manufacture of a pharmaceutical dosage form according to any of claims/embodiments (1) to (50) characterized in that the minimum spraying time is deduced from the asymptotic dependency of the achieved coating uniformity (expressed as relative standard deviation RSD) of the coating time determined by a series of coating experiments, preferably at three coating experiments with sampling at various coating times, preferably with sampling with at least two coating times per experiment, preferably using optimized parameters for drum load, preferably at a drum load of 60 to 90%, preferably 60 to 80% of the nominal drum capacity and drum speed preferably at a peripheral speed of the coating drum which exceeds 0.3 m/s, preferably peripheral speed of the coating drum exceeds 0.4 m/s, more preferably peripheral speed of the coating drum exceeds 0.6 m/s.

(52) The invention further provides a method to determine the endpoint of the coating process in the process for the manufacture of a pharmaceutical dosage form according to any of claims/embodiments (1) to (50) characterized in that the endpoint is determined by in-line Raman spectroscopy using a PhAT probe and SNV preprocessed spectra in the spectral region from 1540 $cm^{-1}$ to 1750 $cm^{-1}$.

(53) The invention further provides a method to determine the endpoint of the coating process in the process for the manufacture of a pharmaceutical dosage form in form of a bilayer tablet according to any of claims/embodiments (1) to (50) characterized in that the endpoint is determined by in-line Raman spectroscopy using a PhAT probe and SNV preprocessed spectra in the spectral region from 1540 $cm^{-1}$ to 1750 $cm^{-1}$.

(54) The invention further provides a method to determine the endpoint of the coating process in the process for the manufacture of a pharmaceutical dosage form in form of a bilayer tablet comprising nifedipine according to any of claims/embodiments (1) to (50) characterized in that the endpoint is determined by in-line Raman spectroscopy using a PhAT probe and SNV preprocessed spectra in the spectral region from 1540 $cm^{-1}$ to 1750 $cm^{-1}$.

(55) The invention further provides a method to determine the endpoint of the coating process in the process for the manufacture of a pharmaceutical dosage form in form of a osmotic system bilayer tablet comprising nifedipine according to any of claims/embodiments (1) to (50) characterized in that the endpoint is determined by in-line Raman spectroscopy using a PhAT probe and SNV preprocessed spectra in the spectral region from 1540 $cm^{-1}$ to 1750 $cm^{-1}$.

(56) The invention further provides a pharmaceutical dosage form comprising nifedipine and candesartan cilexetil obtainable, preferably obtained by a manufacturing process according to any of claims/embodiments (1) to (50) characterized in that nifedipine is released in the body in a controlled (modified) manner and the candesartan cilexetil is released rapidly (immediate release (IR)).

(57) The invention further provides a pharmaceutical dosage form comprising nifedipine and candesartan cilexetil obtainable, preferably obtained by a manufacturing process according to any of claims/embodiments (1) to (50) characterized in that nifedipine is released in the body in a controlled (modified) manner and the candesartan cilexetil is released rapidly (immediate release (IR)) and that the dosage form is based on a osmotic system, preferably osmotic two chamber system.

(58) The invention further provides a pharmaceutical dosage form comprising nifedipine and candesartan cilexetil and a diuretic obtainable, preferably obtained by a manufacturing process according to any of claims/embodiments (1) to (50) characterized in that nifedipine is released in the body in a controlled (modified) manner and the candesartan cilexetil is released rapidly (immediate release (IR)).

(59) The invention further provides a pharmaceutical dosage form comprising nifedipine and candesartan cilexetil obtainable, preferably obtained by a manufacturing process according to any of claims/embodiments (1) to (50) characterized in that nifedipine is released in the body in a controlled (modified) manner and the candesartan cilexetil is released rapidly (immediate release (IR)) further characterized in that AV<15%, <12%, <10%, if 10 tablets are investigated for individual content.

(60) The invention further provides a pharmaceutical dosage form comprising nifedipine and candesartan cilexetil obtainable, preferably obtained by a manufacturing process according to any of claims/embodiments (1) to (50) characterized in that nifedipine is released in the body in a controlled (modified) manner and the candesartan cilexetil is released rapidly (immediate release (IR)) further characterized in that AV<15%, <12%, <10% if 30 tablets are investigated for individual content.

(61) The invention furthermore provides a medicament comprising a pharmaceutical dosage form according to one or more of claims/embodiments (56) to (60).

(62) The invention furthermore provides the use of a pharmaceutical dosage form according to one or more of claims/embodiments (56) to (60) for the prophylaxis, secondary prophylaxis and/or treatment of disorders.

(63) The invention furthermore provides the use of a pharmaceutical dosage form according to one or more of claims/embodiments (56) to (60) for preparing a medicament for the prophylaxis, secondary prophylaxis and/or treatment of disorders.

(64) The invention furthermore provides the use of a pharmaceutical dosage form according to one or more of claims/embodiments (56) to (60) for the prophylaxis, secondary prophylaxis and/or treatment of cardiovascular disorders.

(65) The invention furthermore provides the use of a pharmaceutical dosage form according to one or more of claims/embodiments (56) to (60) for the prophylaxis, secondary prophylaxis and/or treatment of hypertension.

(66) The invention furthermore provides the use of nifedipine or nisoldipine and an angiotensin II antagonist and/or a diuretic for preparing a pharmaceutical dosage form.

(67) The invention furthermore provides a manufacturing process according to one or more of claims/embodiments (1) to (50) characterized in that the manufacturing process for each individual layer of the mantle coating typically comprises the steps of
  providing a defined amount of tablets (or tablet cores) in the coating drum
  pre-warming the tablets until the tablets in the coater or the exhaust air has reached a defined minimal temperature, preferably until the exhaust air has reached a defined minimal temperature, such as "at least 40° C."
  spraying the coating suspension onto the moving tablet bed in the coater
  optionally further drying, polishing and/or cooling the coated tablets until the tablets in the coater or the exhaust air has reached a defined maximal temperature, preferably until the exhaust air has reached a defined maximal temperature, such as "less than 35° C." for at least further 10 minutes and until the exhaust air temperature has reached 35° C. whatever is longer.

The spraying step for colour coatings is typically performed until a predefined amount of coating suspension has been used. This amount typically includes an overage of 0-20%, preferably 5-15% in order to compensate spraying losses. The required overages mainly depend on the coating equipment and a skilled operator will be able to define suitable overages for colour coating processes in a specific equipment.

In the sense of the present invention the dosage forms mentioned above in all embodiments are based preferably on an osmotic system, preferably an osmotic two chamber system.

Wherever in the above-mentioned embodiments it is defined that the spraying process is performed substantially continuously over at least a defined number of hours or at least over a scale and equipment specific minimum spraying time, it is meant that the actual coating time should be within a range defined by that time as a minimum and the two-fold, preferably the 1.5-fold, preferably the 1.4-fold, more preferably the 1.2-fold, most preferably the 1.1-fold of that time as a maximum.

Furthermore the invention relates to
1. Process for the manufacture of a pharmaceutical dosage form comprising nifedipine in the core and candesartan cilexetil in the active coating layer with mean candesartan cilexetil content of 95-105%, characterized in that the candesartan cilexetil active coating process is performed until the desired amount of candesartan cilexetil has been applied to the tablets as determined by in-line NIR or Raman spectroscopy.
2. Process for the manufacture of a pharmaceutical dosage form according to claim 1 characterized in that in-line Raman spectroscopy is utilized using a PhAT probe and SNV preprocessed spectra in the spectral region from 1540 $cm^{-1}$ to 1750 $cm^{-1}$.
3. Process for the manufacture of a pharmaceutical dosage form according to any of claims 1 to 2 characterized in that the mean candesartan cilexetil content in the active coating layer is 98.5-101.5%.
4. Process for the manufacture of a pharmaceutical dosage form according to any of claims 1 to 3 characterized in that the inter-tablet variability of the candesartan cilexetil content is less than 5%, characterized in that the spraying process is performed substantially continuously over at least 3 hours and optionally over the two-fold, preferably the 1.5-fold, preferably the 1.4-fold, more preferably the 1.2-fold, most preferably the 1.1-fold of that time as a maximum spraying time.
5. Process for the manufacture of a pharmaceutical dosage form according to any of claims 1 to 4 characterized in that the inter-tablet variability of the candesartan cilexetil content is less than 5%, characterized in that the spraying process is performed substantially continuously over at least a scale and equipment specific minimum spraying time and optionally over the two-fold, preferably the 1.5-fold, preferably the 1.4-fold, more preferably the 1.2-fold, most preferably the 1.1-fold of that time as a maximum spraying time.
6. Process for the manufacture of a pharmaceutical dosage form according to any of claims 4 to 5 characterized in that the spraying process is performed using at least 4 spray nozzles.

7. Process for the manufacture of a pharmaceutical dosage form according to any of claims 4 to 6 characterized in that the peripheral speed of the coating drum exceeds 0.3 m/s.
8. Process for the manufacture of a pharmaceutical dosage form according to any of claims 4 to 7 characterized in that the spraying step of the candesartan cilexetil active coating process is performed at a drum load of 60 to 90%.
9. Use of in-line Raman spectroscopy to determine the endpoint of the coating process according to any of claims 1 to 8 characterized in that the endpoint is determined by in-line Raman spectroscopy using a PhAT probe and SNV preprocessed spectra in the spectral region from 1540 $cm^1$ to 1750 $cm^{-1}$.
10. Method to determine the scale and equipment specific minimum spraying time characterized in that the minimum spraying time is deduced from the asymptotic dependency of the achieved coating uniformity (expressed as relative standard deviation RSD) of the coating time determined by a series of coating experiments, preferably at three coating experiments with sampling at various coating times, preferably with sampling with at least two coating times per experiment, preferably using optimized parameters for drum load, preferably at a drum load of 60 to 90% of the nominal drum capacity and drum speed preferably at a peripheral speed of the coating drum which exceeds 0.3 m/s.
11. Pharmaceutical dosage form comprising nifedipine in the core and candesartan cilexetil in the active coating layer with a mean candesartan cilexetil content of 95-105% obtainable, preferably obtained by a process according to any of claims 1 to 8, characterized in that nifedipine is released in the body in a controlled (modified) manner and the candesartan cilexetil is released rapidly (immediate release (IR)).

The pharmaceutical dosage forms according to the invention comprise nifedipine and candesartan cilexetil and optionally a diuretic, wherein the candesartan cilexetil and optionally the diuretic is released rapidly (IR) and nifedipine is release in delayed form and which thus corresponds to the release behaviour of the known individual formulations.

The pharmaceutical dosage forms according to the invention are solid, administered orally and preferably constructed on the basis of an osmotic active ingredient release system comprising nifedipine.

In the pharmaceutical dosage form according to the invention, nifedipine is located in the core, preferably constructed on the basis of an osmotic active ingredient release system, and the candesartan cilexetil and optionally a diuretic is located in a mantle coating around the core. In embodiments comprising candesartan cilexetil and a diuretic in the mantle coating, the candesartan cilexetil and the diuretic may be located in the same layer of the mantle coating or in separate layers, applied in succession, of the mantle coating. Wherein the diuretic is selected from the group consisting of acetazolamide, dichlorphenamide, methazolamide, furosemide, torasemide, bumetanide, etacrynic acid, piretanide, amiloride, triamterene, spironolactone, potassium canrenoate, eplerenone, hydrochlorothiazide, chlorthalidone, xipamide, metolazone, mefruside and indapamide.

The active ingredients can be present in the pharmaceutical dosage form according to the invention in crystalline, partially crystalline, partially amorphous or amorphous form. Preferably, the active ingredients nifedipine and candesartan cilexetil are present in crystalline or predominantly crystalline form. In a preferred embodiment, one or more of the active ingredients are present in micronized form, i.e. nifedipine is present in micronized form and/or candesartan cilexetil is in micronized form. In a particularly preferred embodiment, all active ingredients are present in crystalline or predominantly crystalline form and in micronized form.

Here, nifedipine preferably has an average particle size $X_{50}$ of from 2 to 6 μm and an $X_{90}$ value (90% portion) of less than 12 μm. Candesartan cilexetil preferably has an average particle size $X_{50}$ of from 0.5 to 8 μm, preferably from 1 to 5 μm, and an $X_{90}$ value (90% portion) of less than 20 μm, preferably of 3 to 10 μm, most preferably of 4 to 8 μm. The $X_{50}$ and $X_{90}$ values always refer to the particle size distribution, determined by laser diffractometry and stated as volume distribution.

Nifedipine is used in a dose of 10-90 mg, preferably in a dose of 20 mg, 30 mg, or 60 mg. Candesartan cilexetil is used in a dose of 2-32 mg, preferably in a dose of 4 mg, 8 mg, 16 mg or 32 mg. Thus, the pharmaceutical form according to the invention preferably comprises nifedipine in dosages of 20, 30 or 60 mg, and candesartan cilexetil in dosages of 4, 8, 16 or 32 mg. Particularly preferred dose strength combinations are: 30 mg nifedipine+8 mg candesartan cilexetil, 30 mg nifedipine+16 mg candesartan cilexetil, 60 mg nifedipine+16 mg candesartan cilexetil, and 60 mg nifedipine+32 mg candesartan cilexetil.

In case the pharmaceutical dosage form also comprises a diuretic, the diuretic is preferably selected from hydrochlorothiazide in doses of 12.5 mg and 25 mg and chlorthalidone in doses of 12.5 mg, 25 mg and 50 mg.

The core of the pharmaceutical dosage form according to the invention may be a delayed-release tablet, a mantle tablet, a coated tablet, a coated mantle tablet, a delayed-release capsule or an osmotic active ingredient release system, coated with the mantle coating according to the invention comprising candesartan cilexetil and optionally a diuretic. The core is preferably an osmotic active ingredient release system, most preferably an osmotic two-chamber system comprising
    a core having an active ingredient layer, comprising
        5 to 50% of the active ingredient nifedipine,
        40 to 95% of one or more osmotically active polymers (preferably polyethylene oxide having a viscosity of 40 to 100 mPa·s as determined in a 5% strength aqueous solution at 25° C.),
    and an osmosis layer, comprising
        40 to 95% of one or more osmotically active polymers (preferably polyethylene oxide having a viscosity of 5000 to 8000 mPa·s as determined in a 1% strength aqueous solution at 25° C.),
        5 to 40% of an osmotically active additive (preferably sodium chloride),
    and also a coat consisting of a water-permeable material (preferably consisting of cellulose acetate or a mixture of cellulose acetate and polyethylene glycol) which is impermeable for the components of the core and has at least one orifice.

The osmotic two-chamber system may be manufactured by a process comprising
    mixing and granulating the components of the active ingredient layer
    mixing and granulating the components of the osmosis layer,
    compressing both sets of granules on a bilayer tablet press to give a bilayer tablet,
    coating the resulting inner core with the coat and providing the coat, on the active ingredient side, with one or more orifices.

The mantle coating of the dosage forms according to the invention comprises candesartan cilexetil, optionally a diuretic and at least one film-forming polymer. The film-forming polymer may be chosen such that it is suitable for the rapid release of active ingredients. In embodiments comprising candesartan cilexetil and a diuretic in the mantle coating, the candesartan cilexetil and the diuretic may be located in the same coating layer or in separate coating layers, applied in succession.

Suitable film-forming polymers are cellulose derivatives, synthetic polymers and mixtures thereof.

Cellulose derivatives that may be mentioned are methylcellulose (MC), hydroxymethylpropylcellulose (HPMC), hydroxypropylcellulose (HPC), carboxymethyl-cellulose-sodium (Na-CMC), hydroxyethyl-cellulose (HEC) and mixtures thereof.

Synthetic polymers that may be mentioned are polyvinylpyrrolidone (povidone, PVP), vinylpyrrolidone-vinyl acetate copolymer (copovidone), polyvinyl alcohol (PVA), polyvinyl acetate (PVAc), partially hydrolyzed polyvinyl alcohol, polyvinyl alcohol-polyethylene glycol copolymers (PVA-co-PEG) and mixtures thereof.

Preferred film-forming polymers are polyvinyl alcohol (PVA), polyvinyl acetate (PVAc), partially hydrolyzed polyvinyl alcohol, polyvinyl alcohol-polyethylene glycol copolymers (PVA-PEG co-polymer) and mixtures thereof.

A preferred film-forming polymer is in particular partially hydrolyzed polyvinyl alcohol.

Preference is furthermore given in particular to the commercially available preparations below, "ready-to-use film coating systems" which already comprise further pharmaceutical excipients and are simply dispersed in water.

Kollicoat IR white (BASF PVA-co-PEG-based finished coating with white pigment), composition: Kollicoat IR (PVA-co-PEG), Kollidon VA64 (copovidone), kaolin, sodium lauryl sulphate, titanium dioxide.

Sepifilm IR Colorless (SEPPIC PVA-co-PEG-based finished coating without pigments), composition: Kollicoat IR (PVA-co-PEG), polydextrose, kaolin, polyethylene glycol (PEG 400).

Opadry II 85F19250 Clear (Colorcon PVA-based finished coating), composition: partially hydrolyzed polyvinyl alcohol, talc, polyethylene glycol (PEG 3350), polysorbate 80 (Tween 80). This finished coating is particularly preferred.

The mantle coating can also be prepared from the individual components, for example from the following commercially available preparations: BASF Kollicoat IR (PVA-co-PEG), BASF Kollidon VA64 (copovidone), Merck Emprove (PVA).

The mantle coating may comprise further excipients such as, for example, wetting agents (for example sodium lauryl sulphate, quaternary ammonium compounds, lecithin (in particular soya lecithin), polysorbates (in particular Polysorbat 80, synonym Tween 80)), pigments (for example titanium dioxide, talc), colour pigments (for example iron oxide red, yellow or black or mixtures thereof), release agents (for example kaolin, talc, finely divided silica, magnesium stearate, glycerol monostearate), and/or plasticizers (for example polyethylene glycol (in particular polyethylene glycol 400, polyethylene glycol 3350), polypropylene glycol, propylene glycol, glycerol, triacetin, triethyl citrate).

In the mantle coating, the proportion of candesartan cilexetil, if appropriate together with the proportion of diuretic, is from 10 to 50%, preferably from 20 to 40%, particularly preferably 40%. The proportion of film-forming polymer is from 20 to 75%, preferably from 25 to 60%, particularly preferably about 30 to 45%, the proportion of pigment is from 0 to 20%, the proportion of wetting agent is from 0 to 3%, preferably from 1 to 2%, based on the dry weight of the mantle coating. When finished coatings are used, the proportion of candesartan cilexetil, if appropriate together with the proportion of diuretic, is from 10 to 50%, preferably from 20 to 40%, particularly preferably 40%, and the proportion of finished coating is from 50 to 90%, preferably from 60 to 80%, particularly preferably 60%. Here, the percentages for the mantle coating refer to the active ingredient coating without any colouring coating that may be present in addition.

The aqueous coating suspension comprises preferably about 20 to about 30%, particularly preferably 25-30%, of solids, based on the total weight of the coating suspension. The aqueous coating suspension can preferably be manufactured by dispersing a powder mixture comprising the active ingredient and the ready-to-use film coating system in water using a dissolver strirrer. Alternatively, the individual components can be added consecutively to one or more portions of purified water and finally be joined and mixed using suitable equipment and dispersion procedures well known in the art.

The weight of the mantle coating in the dosage form according to the invention is generally from 10 to 300 mg, preferably from 20 to 225 mg. If candesartan cilexetil is the only active ingredient that is present in the active ingredient layer, the weight of the mantle coating in the dosage form according to the invention is preferably from 20 to 80 mg, more preferably 20, 40 or 80 mg. Here, the weight of the mantle coating comprises only that of the active ingredient coating, without any colouring coating that may be present in addition.

The thickness of the mantle coating in the dosage form according to the invention is generally from 50 to 500 µm, preferably from 50 to 250 µm, particularly preferably from 80 to 200 µm. Here, the thickness of the mantle coating comprises only that of the active ingredient coating, without any colouring coating that may be present in addition.

A further coating without active ingredient, for example a photoprotective and/or colouring coating, can be applied to the mantle coating of the dosage form according to the invention if required. Excipients suitable for this purpose are, in principle, the same excipients as those used for the mantle coating. Materials suitable for this purpose are in particular polymers such as polyvinyl alcohol, hydroxypropylcellulose or hydroxypropylmethylcellulose, where appropriate in combination with suitable plasticizers such as, for example, polyethylene glycol and pigments such as, for example, titanium dioxide or iron oxides.

Preference is given in particular to the following commercially available preparations, "ready-to-use film coating systems" which already comprise further pharmaceutical excipients and which are simply dispersed in water, such as, for example, Opadry II 85F230009 Orange, Opadry II 85F26912 Brown, Opadry II 85F250022 Red (Colorcon PVA-based ready-to-use coating systems), composition: partially hydrolyzed polyvinyl alcohol, talc, polyethylene glycol (PEG 3350), titanium dioxide, red iron oxide, yellow iron oxide and polysorbate 80 (Tween 80).

Furthermore, the tablets can be imprinted with an suitable ink (such as Opacode qualities provided by Colorcon) in order to facilitate drug identification.

Each individual layer of the mantle coating may be manufactured by a pharmaceutical film coating process using a suitable coating equipment. Preferably the coating equipment is a drum coater with a perforated coating drum.

The manufacturing process for each individual layer of the mantle coating typically comprises the steps of
- providing a defined amount of tablets (or tablet cores) in the coating drum
- pre-warming the tablets
- spraying the coating suspension onto the moving tablet bed in the coater
- optionally further drying, polishing and/or cooling the coated tablets.

Each of these manufacturing steps is typically performed until a predefined criterion is reached. The pre-warming step is typically performed until the tablets in the coater or the exhaust air has reached a defined minimal temperature, preferably until the exhaust air has reached a defined minimal temperature, such as "at least 40° C.". The final cooling step is typically performed until the tablets in the coater or the exhaust air has reached a defined maximal temperature, preferably until the exhaust air has reached a defined maximal temperature, such as "less than 35° C.". The criterion for the cooling step can also be a combined criterion reflecting a minimal time period and a maximal temperature of the exhaust air to be achieved, such as "for at least further 10 minutes and until the exhaust air temperature has reached 35° C. whatever is longer".

The spraying step for colour coatings is typically performed until a predefined amount of coating suspension has been used. This amount typically includes an overage of 0-20%, preferably 5-15% in order to compensate spraying losses. The required overages mainly depend on the coating equipment and a skilled operator will be able to define suitable overages for colour coating processes in a specific equipment.

Special emphasis is given to the endpoint determination and the process parameters of the spraying step of the active coating process. The spraying step for active coatings according to the invention can be performed until a predefined amount of coating suspension has been used, or, until a desired increase in tablet weight has been achieved, or, until a predefined coating thickness has been achieved, or, until a desired amount of active ingredient has been coated onto the tablets, or, until a optionally weighed combination of these criteria has been reached. The increase in tablet weight can be monitored at-line using a balance; the increase in film thickness can be monitored at-line using a micrometer gauge or using Terahertz Pulsed Imaging, the increase in active content can be monitored at-line using HPLC assay or at-line and/or in-line using spectroscopic techniques such as NIR and/or Raman spectroscopy. If using at-line technologies, the coating process may be stopped during the investigation of the samples. This is a very time-consuming process. For that reason, in-line technologies are very much preferred.

Surprisingly, in-line spectroscopic monitoring using either NIR or Raman spectroscopy is even more accurately predicting the coating endpoint as respective at-line methods. Raman spectroscopy furthermore, surprisingly, combines several advantages such as a low spectroscopic signal variability, high accuracy, short measuring intervals and high model robustness.

According to the invention, it is thus preferred that the candesartan cilexetil active coating process is performed until the desired amount of candesartan cilexetil has been applied to the tablets as determined by in-line NIR or Raman spectroscopy, preferably by in-line Raman spectroscopy.

Most preferably, the candesartan cilexetil active coating process is performed until the desired amount of candesartan cilexetil has been applied to the tablets as determined by in-line Raman spectroscopy using a PhAT probe and SNV preprocessed spectra in the spectral region from 1540 $cm^{-1}$ to 1750 $cm^{-1}$.

The process parameters of the active coating process are selected in a way that reduces process variability as much as possible. The process parameters may be adapted during the spraying process or be kept constant during the spraying step. Preferably, the process parameters are kept constant during the spraying step. Below and in the examples, the process parameters are provided in general terms and also in detail for the specific equipment used by the present inventors. The process parameters depend on the type and the scale of the equipment used. When using different equipment, a skilled operator will be able to select appropriate process parameters for the selected equipment based on the general disclosure provided below.

Surprisingly the present inventors have found that by the selection of the following parameters the desired coating uniformity could be achieved. Namely, an inter-tablet variability of the candesartan cilexetil content of less than 5%, preferably less than 4.8%, more preferably less than 4.5%, and mean candesartan cilexetil contents of 95-105%, preferably 98.5-101.5% are reproducibly and reliably achieved. According to the invention, it is preferred that the spraying step of the candesartan cilexetil active coating process is performed at a drum load of 50 to 100%, preferably 60 to 90%, more preferably 60 to 80% of the nominal drum capacity. For example, in case a Bohle BFC 5 lab scale coater is used, it is preferred that the spraying step of the candesartan cilexetil active coating process is performed at a drum load of 2.5 to 4.0 kg, preferably 3.0 to 3.5 kg. In case a Bohle BFC 50 pilot scale coater is used, it is preferred that the spraying step of the candesartan cilexetil active coating process is performed at a drum load of 35 to 45 kg, preferably 37 to 43 kg. In case a Bohle BFC 400 commercial scale coater is used, it is preferred that the spraying step of the candesartan cilexetil active coating process is performed at a drum load of 220 to 280 kg, preferably 240 to 260 kg. In the context of the present invention drum load refers to the weight of tablet cores to be coated and does not include the amount of film coat applied during the coating process.

According to the invention, it is preferred that the spraying step of the candesartan cilexetil active coating process is performed at a maximized drum speed, the highest drum speed that still results in a continuously flowing tablet bed. It is further preferred, that the peripheral drum speed exceeds 0.3 m/s, more preferably peripheral drum speed exceeds 0.4 m/s, more preferably peripheral drum speed exceeds 0.6 m/s. For example, in case a Bohle BFC 5 lab scale coater is used, it is preferred that the spraying step of the candesartan cilexetil active coating process is performed at a drum speed of 18-20 rpm, preferably 20 rpm. In case a Bohle BFC 50 pilot scale coater is used, it is preferred that the spraying step of the candesartan cilexetil active coating process is performed at a drum speed of 13-14 rpm, preferably 14 rpm. In case a Bohle BFC 400 commercial scale coater is used, it is preferred that the spraying step of the candesartan cilexetil active coating process is performed at a drum speed of 8-9 rpm, preferably 9 rpm.

The spray rate and the spraying time of a coating time are linked to each other, as the same amount of coating suspension can be sprayed at a high rate in a short period of time or at a lower rate in a longer period of time. It has surprisingly been found that the coating uniformity can be optimized when a scale and equipment specific minimum spraying time is used. Performing a number of coating experiments, preferably using already optimized parameters for drum load and drum speed, and investigating the relative standard deviation of the candesartan cilexetil content after various coating times, an asymptotic dependency of the achieved coating uniformity (expressed as relative standard deviation RSD) of the coating time is observed. The respective scale and equipment specific minimum spraying time for the Bohle BFC 400 commercial scale coater can exemplarily deduced from FIG. 1 (data according to example 7). The relative standard deviation of the candesartan cilexetil content can be reliably and reproducibly controlled to values below 6%, preferably below 5% or even less if the spraying time exceeds 6 hours whereas further extension of spraying time does not significantly improve the content uniformity. Thus, it is preferred to select a substantially constant spraying rate throughout the spraying step of the active coating process in such a way, that the spraying time exceeds the scale and equipment specific minimum spraying time, e.g. 6 hours in the case of the BFC 400 commercial scale coater. It has surprisingly been found, that the required spraying time is scale and equipment specific, but substantially independent of the amount of coating to be applied.

According to the invention it is preferred that the spraying step of the candesartan cilexetil active coating process is performed using more than one spray nozzle, preferably at least two spray nozzles, most preferably at least 4 spray nozzles.

According to the invention, it is preferred that the spraying step of the candesartan cilexetil active coating process is performed at a spraying rate that results in a spraying time exceeding the scale and equipment specific minimum spraying time of the selected equipment. For example, in case a Bohle BFC 5 lab scale coater is used, it is preferred that the spraying step of the candesartan cilexetil active coating process is performed at a spraying rate that results in a spraying time exceeding 3 hours. In case a Bohle BFC 50 pilot scale coater is used, it is preferred that the spraying step of the candesartan cilexetil active coating process is performed at a spraying rate that results in a spraying time exceeding 4 hours. In case a Bohle BFC 400 commercial scale coater is used, it is preferred that the spraying step of the candesartan cilexetil active coating process is performed at a spraying rate that results in a spraying time exceeding 6 hours. Wherever it is defined that the spraying process is performed substantially continuously over at least a defined number of hours or at least over a scale and equipment specific minimum spraying time, it is meant that the actual coating time should be within a range defined by that time as a minimum and the two-fold, preferably the 1.5-fold, preferably the 1.4-fold, more preferably the 1.2-fold, most preferably the 1.1-fold of that time as a maximum.

It is therefore another aspect of the present invention to provide a method to determine the scale and equipment specific minimum spraying time characterized in that the minimum spraying time is deduced from the asymptotic dependency of the achieved coating uniformity (expressed as relative standard deviation RSD) of the coating time determined by a series of coating experiments with sampling at various coating times, preferably using optimized parameters for drum load and drum speed.

The spray pressure (atomizing air) and the forming air pressure are selected in a way that a homogeneous oval shaped spray pattern is achieved. Further process parameters, e.g. spray pressure, air flow, air temperatures etc., of the spraying step of the active coating steps are disclosed in the experimental part for each scale of pharmaceutical coating processes. The inlet air temperature is preferably maintained <60° C. and more preferably in a way that the resulting exhaust air temperature is in a range of 35-45 C, preferably in a range of 40-44° C.

Furthermore, it is preferred to combine some or all of the preferred process parameters mentioned above in order to minimize the relative standard deviation and thus improve the content uniformity to an optimum. In other words, it is for example particularly preferred that the spraying step of the candesartan cilexetil active coating process is performed at a drum load of 60 to 90%, preferably 60 to 80% of the nominal drum capacity, at a maximized drum speed, and at a spraying rate that results in a spraying time exceeding the scale and equipment specific minimum spraying time of the selected equipment.

Furthermore, it is preferred to combine some or all of the preferred process parameters mentioned above in order to minimize the relative standard deviation and thus improve the content uniformity to an optimum. In other words, it is for example particularly preferred that the spraying step of the candesartan cilexetil active coating process is performed at a drum load of 50% to 100%, preferably 60 to 90%, preferably 60 to 80% of the nominal drum capacity, at a maximized drum speed that exceeds 0.3 m/s, more preferably peripheral drum speed exceeds 0.4 m/s, more preferably peripheral drum speed exceeds 0.6 m/s and at a spraying rate that results in a spraying time exceeding the scale and equipment specific minimum spraying time of the selected equipment.

Further, it is preferred to combine an selected set of preferred process parameters with a preferred method of defining the endpoint criterion for the spraying step in order to improve the content uniformity with regard to both, control of the mean of individual contents in a range of 98.5-101.5% and the respective standard deviation below 5%, thus resulting in acceptance values (AV) reliably and reproducibly below 15% even if only n=10 tablets are investigated (stage 1 testing). In other words, it is for example preferred that the spraying step of the candesartan cilexetil active coating process is performed at a drum load of 50 to 100% of the nominal drum capacity, at a maximized drum speed, and at a spraying rate that results in a spraying time exceeding the scale and equipment specific minimum spraying time of the selected equipment, until the desired amount of candesartan cilexetil has been applied to the tablets as determined by in-line NIR and/or Raman spectroscopy.

Further, it is preferred to combine an selected set of preferred process parameters with a preferred method of defining the endpoint criterion for the spraying step in order to improve the content uniformity with regard to both, control of the mean of individual contents in a range of 98.5-101.5% and the respective standard deviation below 5%, thus resulting in acceptance values (AV) reliably and reproducibly below 15% even if only n=10 tablets are investigated (stage 1 testing). In other words, it is for example preferred that the spraying step of the candesartan cilexetil active coating process is performed at a drum load of 50 to 100% of the nominal drum capacity, at a maximized drum speed that exceeds 0.3 m/s, more preferably peripheral drum speed exceeds 0.4 m/s, more preferably peripheral drum speed exceeds 0.6 m/s and at a spraying rate that results in a spraying time exceeding the scale and equipment specific minimum spraying time of the selected equipment, until the desired amount of candesartan cilexetil has been applied to the tablets as determined by in-line NIR and/or Raman spectroscopy. Wherever it is defined that the spraying process is performed substantially continuously over at least a defined number of hours or at least over a scale and equipment specific minimum spraying time, it is meant that the actual coating time should be within a range defined by that time as a minimum and the two-fold, preferably the 1.5-fold, preferably the 1.4-fold, more preferably the 1.2-fold, most preferably the 1.1-fold of that time as a maximum.

It is furthermore particularly preferred that the spraying step of the candesartan cilexetil active coating process is performed at a drum load of 60 to 90%, preferably 60 to 80% of the nominal drum capacity, at a maximized drum speed, and at a spraying rate that results in a spraying time exceeding the scale and equipment specific minimum spraying time of the selected equipment, until the desired amount of candesartan cilexetil has been applied to the tablets as determined by in-line Raman spectroscopy using a PhAT probe and SNV preprocessed spectra in the spectral region from $1540$ $cm^{-1}$ to $1750$ $cm^{-1}$.

It is furthermore particularly preferred that the spraying step of the candesartan cilexetil active coating process is performed at a drum load of 60 to 90%, preferably 60 to 80% of the nominal drum capacity, at a maximized drum speed that exceeds 0.3 m/s, more preferably peripheral drum speed exceeds 0.4 m/s, more preferably peripheral drum speed exceeds 0.6 m/s and at a spraying rate that results in a spraying time exceeding the scale and equipment specific minimum spraying time of the selected equipment, until the desired amount of candesartan cilexetil has been applied to the tablets as determined by in-line Raman spectroscopy using a PhAT probe and SNV preprocessed spectra in the spectral region from $1540$ $cm^{-1}$ to $1750$ $cm^{-1}$.

Advantageously, the active coating process according to the invention has a very low loss during spraying of 0.5-3%, preferably 0.5-2%. Thus, more than 97%, preferably more than 98% of the active coating suspension sprayed into the coater are typically coated onto the tablets.

The pharmaceutical dosage forms according to the invention meets the pharmacopoeia requirements of content uniformity as defined for example in the general chapter 2.9.40 Uniformity of dosage units of the European Pharmacopoeia (Ph. Eur.).

The pharmaceutical dosage forms according to the invention exhibit a mean candesartan cilexetil content within the range of 95-105%, preferably within the range of 96-104%, more preferably within the range of 97-103%, even more preferably within the range of 97.5-102.5%, in particular preferably within the range of 98-102%, and most preferably within the range of 98.5-101.5%.

The pharmaceutical dosage forms according to the invention exhibit a standard deviation of the candesartan cilexetil content of less than 7%, preferably less than 6.5%, more preferably less than 6%, even more preferably less than 5.5%, in particular preferably less than 5%, and most preferably less than 4.5%.

The pharmaceutical dosage forms according to the invention exhibit an acceptance value according to Ph. Eur. general chapter 2.9.40 of less than 15% when n=30 tablets are investigated (stage 2 testing). Preferably, the pharmaceutical dosage forms according to the invention exhibit an acceptance value according to Ph. Eur. general chapter 2.9.40 of less than 15% when n=10 tablets are investigated (stage 1 testing).

Furthermore, the process according to the invention may be validated using the preferred process parameters and the preferred methods of defining the end criterion for the spraying step as design space. Thus, the pharmaceutical dosage forms according to the invention reproducibly and reliably exhibit an acceptance value according to Ph. Eur. general chapter 2.9.40 of less than 15% when n=30 tablets are investigated (stage 2 testing). Preferably, the pharmaceutical dosage forms according to the invention reproducibly and reliably exhibit an acceptance value according to Ph. Eur. general chapter 2.9.40 of less than 15% when n=10 tablets are investigated (stage 1 testing).

Furthermore, the pharmaceutical dosage form according to the invention, also fulfils the Ph. Eur. Content uniformity requirement that all individual assays should be in the range of 75% to 125%.

The pharmaceutical dosage forms according to the invention have a very low friability of less than 0.5%, preferably less than 0.1%, particularly preferably less than 0.01%, or even no measurable friability, based on the weight of the dosage form, as determined for example according to USP 31 <1216> Tablet Friability.

When tested for resistance to crushing using a suitable instrument for testing tablets (for example Schleuniger Type 6D or Type 8M, Dr. Schleuniger Pharmatron AG, Solothurn, Switzerland), the pharmaceutical dosage form according to the invention shows a resistance to crushing of greater than 200 N, preferably greater than 300 N. In a particularly preferred embodiment, during the test for resistance to crushing there is neither breaking nor cracking of the mantle coating, but at most a slight plastic deformation, up to 449 N.

In the disintegration test (for example according to USP 31 <701> Disintegration), using purified water as medium at 37° C., the mantle coating of the pharmaceutical dosage form according to the invention can be detached completely from the core within a period of 25 minutes, preferably within 15 minutes, particularly preferably within 10 minutes.

In the test for in-vitro release, the pharmaceutical dosage form according to the invention releases at least 85% of the nifedipine (based on the declared amount of nifedipine) over a period of at least 4 and at most 24 hours, and less than 20% of the nifedipine within 4 hours, and from 43 to 80%, preferably from 45 to 75%, in particular preferably from 50 to 70% of the nifedipine within 12 hours. The test for in-vitro release for nifedipine is carried out according to the USP release method using apparatus 2 (paddle) at 100 revolutions per minute in 900 mL of phosphate buffer pH 6.8 with addition of 1% sodium lauryl sulphate as the release medium at 37° C.

In the test for in-vitro dissolution, at least 70%, preferably at least 80% of the candesartan cilexetil (based on the declared amount of candesartan cilexetil) are dissolved from the pharmaceutical dosage forms according to the invention within a period of 60 minutes. The test for in-vitro dissolution for candesartan cilexetil is carried out according to the USP dissolution method using apparatus 2 (paddle) at 75 revolutions per minute in 900 mL phosphate buffer pH 6.5 with the addition of 0.7% Tween 20 as the dissolution medium at 37° C.

Thus, the pharmaceutical dosage forms according to the invention exhibit similar in-vitro release profiles of nifedipine as compared to Adalat® GITS formulations of the same dose strength and similar in-vitro dissolution profiles of candesartan cilexetil as compared to Atacand® or Blopress® formulations of the same dose strength.

The pharmaceutical dosage forms are administered orally and comprise an active ingredient combination to be administered once every day.

The invention furthermore provides the use of a pharmaceutical dosage form for the prophylaxis, secondary prophylaxis and/or treatment of disorders.

The invention furthermore provides the use of a pharmaceutical dosage form for preparing a medicament for the prophylaxis, secondary prophylaxis and/or treatment of disorders.

The invention furthermore provides the use of a pharmaceutical dosage form for the prophylaxis, secondary prophylaxis and/or treatment of cardiovascular disorders.

The invention furthermore provides the use of a pharmaceutical dosage form for the prophylaxis, secondary prophylaxis and/or treatment of hypertension.

The invention furthermore provides the use of nifedipine or nisoldipine and an angiotensin II antagonist and/or a diuretic for preparing a pharmaceutical dosage form.

The invention furthermore provides the pharmaceutical dosage form into which, in addition to nifedipine or nisoldipine and the angiotensin II antagonist, a further antihypertensive active ingredient is incorporated. The pharmaceutical dosage form according to the invention is chemically stable and has a shelf life of at least 2 years, preferably at least 3 years when packaged in a suitable primary packaging.

Below, the invention is illustrated by preferred working examples; however, the invention is not limited to these examples. Unless indicated otherwise, all amounts given refer to percent by weight.

EXAMPLES

Example 1

Compositions and Properties of Tablets Comprising Nifedipine+Candesartan Cilexetil All data in mg

| Formulation | 1a | 1b | 1c | 1d | 1e | 1f | 1g | 1h | 1i | 1j | 1k | 1l |
|---|---|---|---|---|---|---|---|---|---|---|---|---|
| Active ingredient layer: | | | | | | | | | | | | |
| nifedipine, micronized | 66.0 | 66.0 | 66.0 | 66.0 | 33.0 | 33.0 | 33.0 | 33.0 | 22.0 | 22.0 | 22.0 | 22.0 |
| HMPC (5 cp) | 16.4 | 16.4 | 16.4 | 16.4 | 8.2 | 8.2 | 8.2 | 8.2 | 5.5 | 5.5 | 5.5 | 5.5 |
| PEO 200 000 | 244.4 | 244.4 | 244.4 | 244.4 | 122.2 | 122.2 | 122.2 | 122.2 | 81.5 | 81.5 | 81.5 | 81.5 |
| magnesium stearate | 0.8 | 0.8 | 0.8 | 0.8 | 0.4 | 0.4 | 0.4 | 0.4 | 0.3 | 0.3 | 0.3 | 0.3 |
| Osmotic layer: | | | | | | | | | | | | |
| HMPC (5 cp) | 8.2 | 8.2 | 8.2 | 8.2 | 4.1 | 4.1 | 4.1 | 4.1 | 3.6 | 3.6 | 3.6 | 3.6 |
| sodium chloride | 47.8 | 47.8 | 47.8 | 47.8 | 23.9 | 23.9 | 23.9 | 23.9 | 21.2 | 21.2 | 21.2 | 21.2 |
| PEO 5 000 000 | 105.8 | 105.8 | 105.8 | 105.8 | 52.9 | 52.9 | 52.9 | 52.9 | 47.0 | 47.0 | 47.0 | 47.0 |
| iron oxide red | 1.6 | 1.6 | 1.6 | 1.6 | 0.8 | 0.8 | 0.8 | 0.8 | 0.7 | 0.7 | 0.7 | 0.7 |
| magnesium stearate | 0.4 | 0.4 | 0.4 | 0.4 | 0.2 | 0.2 | 0.2 | 0.2 | 0.2 | 0.2 | 0.2 | 0.2 |
| Osmotic membrane | | | | | | | | | | | | |
| cellulose acetate | 38.0 | 38.0 | 38.0 | 38.0 | 32.3 | 32.3 | 32.3 | 32.3 | 33.2 | 33.2 | 33.2 | 33.2 |
| PEG 3350 | 2.0 | 2.0 | 2.0 | 2.0 | 1.7 | 1.7 | 1.7 | 1.7 | 1.7 | 1.7 | 1.7 | 1.7 |
| Active coating | | | | | | | | | | | | |
| candesartan cilexetil, micronized | 32.0 | 16.0 | 8.0 | 4.0 | 32.0 | 16.0 | 8.0 | 4.0 | 32.0 | 16.0 | 8.0 | 4.0 |
| Opadry II 85F19250 | 48.0 | 24.0 | 12.0 | 16.0 | 48.0 | 24.0 | 12.0 | 16.0 | 48.0 | 24.0 | 12.0 | 16.0 |
| Colour coating | | | | | | | | | | | | |
| PVA based film coating, e.g. Opadry II 85F230009, 85F26912, 85F250022 | 20.0 | 15.0 | 14.0 | 14.0 | 11.0 | 10.0 | 10.0 | 10.0 | 10.0 | 9.0 | 8.0 | 8.0 |
| Ink for imprinting (optional) | | | | | | | | | | | | |
| White or black imprinting ink, e.g. Opacode | q.s. | q.s. | q.s. | q.s. | q.s. | q.s. | q.s. | q.s. | q.s. | q.s. | q.s. | q.s. |

The actual content of nifedipine is the nominal content +10% overage as a ca. 10% portion of nifedipine remains unreleased due to the intrinsic release properties of the GITS.

Typical size and weight of tablets according to selected examples are as follows:

| example no. | dose strength N + CC* [mg] | diameter [mm] | height [mm] | weight [mg] |
|---|---|---|---|---|
| 1a | 60 + 32 | 11.0 | 6.9 | 631.4 |
| 1b | 60 + 16 | 10.9 | 6.8 | 586.4 |

-continued

| example no. | dose strength N + CC* [mg] | diameter [mm] | height [mm] | weight [mg] |
|---|---|---|---|---|
| 1f | 30 + 16 | 9.4 | 5.4 | 329.7 |
| 1g | 30 + 8 | 9.3 | 5.2 | 309.7 |

*N: nifedipine (nominal content); CC: candesartan cilexetil

The tablets according to examples 1a-11 have a smooth, slightly glossy surface and are optionally imprinted to indicate e.g. the product, manufacturer or dose strength. The tablets are resistant to breaking loads up to 400 N as examined with an hardness tester (Schleuniger Type 6D, Dr. Schleuniger Pharmatron AG, Solothurn, Switzerland). No friability is observed when testing in accordance with USP 31 <1216> Tablet Friability. Testing for disintegration time according to USP 31 <701> Disintegration using purified water as medium at 37° C. showed no complete disintegration as the osmotic release systems stays intact under these conditions. However, after at most 10 minutes, the film coating was completely detached.

The tablets according to examples 1a-11 released max. 20% of the nominal content of nifepidine within 4 hours, 50-70% within 12 hours and at least 85% within 24 hours when tested for release in accordance with USP 31<711> and <724> Dissolution apparatus 2 (paddle apparatus) at 100 rpm (revolutions by minute) and 900 ml of phosphate buffer pH 6.8 with addition of 1.0% of sodium lauryl sulphate as medium at 37° C.

The tablets according to examples 1a-11 provided dissolution of at least 70% of the nominal content of candesartan cilexetil within 60 minutes when tested for release in accordance with USP 31 <711> Dissolution apparatus 2 (paddle apparatus) at 75 rpm (revolutions by minute) and 900 ml of phosphate buffer pH 6.5 with addition of 0.7% of polysorbate 20 (Tween 20) as medium at 37° C.

Active contents of the tablets and samples obtained during release testing can easily investigated using reverse-phase HPLC with UV detection.

Example 2

Manufacturing of the Nifedipine GITS Cores

The components of the active ingredient layer were mixed and subjected to dry granulation. The components of the osmosis layer, too, were mixed and subjected to dry granulation. On a bilayer tablet press, both sets of granules were compressed to give a bilayer tablet. The tablets were coated with a solution of cellulose acetate and polyethylene glycol in acetone and dried. Each tablet was then provided with an orifice of a diameter of 0.9 mm at the active ingredient side using a laser beam.

Cores comprising 22 mg nifedipine (nominal content: 20 mg) obtained in this manner after the process had a diameter of 8.3 mm, a height of 4.2 mm and a weight of for example 216.0 mg±3.9 mg.

Cores comprising 33 mg nifedipine (nominal content: 30 mg) obtained in this manner after the process had a diameter of 8.8 mm, a height of 4.6 mm and a weight of for example 276.6 mg±4.8 mg.

Cores comprising 66 mg nifedipine (nominal content: 60 mg) obtained in this manner after the process had a diameter of 10.6 mm, a height of 6.4 mm and a weight of for example 531.0 mg±3.9 mg.

A plurality of batches of cores of each dose strength are routinely manufactured. Diameters and heights are nearly identical from batch to batches whereas the weight slightly differs from batch to batch. For further processing, the batch specific weight can be determined in order to calculate the actual number of tablets in a given batch.

Example 3

Manufacturing of the Active Coating Suspension

To prepare the active coating suspension, a powder mixture of micronized candesartan cilexetil and Opadry II 85F19250 Clear (4+6 parts by weight) was prepared in a free flow powder mixer (container mixer). The resulting mixture was suspended in purified water (24 parts by weight) using a dissolver stirrer and further stirred for about 45 minutes to result in a homogeneous suspension.

Typical batch sizes and compositions of the active coating suspension are for example:

| Scale | lab | pilot | commercial |
|---|---|---|---|
| micronized candesartan cilexetil | 160 g | 2.4 kg | 20 kg |
| Opadry II 85F19250 Clear | 240 g | 3.6 kg | 30 kg |
| purified water | 960 g | 14.4 kg | 120 kg |
| Total: active coating suspension: | 1.36 kg | 20.4 kg | 170 kg |

The chemical stability of the coating suspension was verified by a comparative stress test: micronized candersartan cilexetil as a solid, an aqueous suspension of micronized candesartan cilexetil, and aqueous suspensions of micronized candesartan cilexetil together with Opadry II 85F19250 Clear in three different ratios were stored at 60° C. for 48 hours. The percentage of the stability indicating impurity Desethyl-Candesartan cilexetil was determined via HPLC. The same batch of micronized candesartan cilexetil has been used for all samples.

| Sample (parts by weight) | Desethyl-Candesartan cilexetil [%] | |
|---|---|---|
| | start | 48 hours |
| micronized candesartan cilexetil (solid) | 0.11 | 0.41 |
| micronized candesartan cilexetil + water (4 + 24) | 0.11 | 0.67 |
| micronized candesartan cilexetil + Opadry + water (2 + 6 + 24) | 0.11 | 0.19 |
| micronized candesartan cilexetil + Opadry + water (4 + 6 + 24) | 0.11 | 0.15 |
| micronized candesartan cilexetil + Opadry + water (8 + 6 + 24) | 0.11 | 0.29 |

Example 4

Manufacturing of the Active Coating Layer in a Lab Scale Coater (Ca. 3-5 Kg Drum Load)

Coater: drum coater BFC 5 from L. B. BOHLE Maschinen+Verfahren GmBH, D-59320 Ennigerloh, fitted with the undivided small drum (dimensions: 316 mm diameter, 480 mm overall length, 360 mm cylindrical length) and a spray arm having 2 ABC spray nozzles.

Coater load: 3-3.5-4 kg of cores according to Example 2, corresponding to 60%-70%-80% of nominal load.1

Drum speed: 16-18-20 rpm (revolutions per minute), corresponding to 0.26-0.30-0.33 m/s peripheral speed Air flow: 160 m$^3$/h Inlet air temperature: 60° C.

Criterion to start spraying: exhaust air temperature >40° C.

Spray arm position: 40°, 1.3 cm

Spray nozzles diameter: 1.0 mm
Spray pressure: 0.8 bar
Forming air pressure: 0.7 bar
Spraying rate: 8-12-16 g/min
Inlet air temperature during spraying: 60° C.
Exhaust air temperature during spraying: ca. 40-50° C. (dependent on the selected process parameters)
Criteria to stop spraying step: the spraying is done until either (a) a predefined spraying time is reached or (b) a predefined amount of coating suspension has been used for spraying or (c) until the tablets in the coater have gained a predefined increase in weight, film thickness and/or candesartan cilexetil content.
Typical total spraying time: ca. 90-240 min
Typical yield of spraying: 97.0-99.0%

A weighed amount of tablet cores is introduced into the coater and pre-warmed until exhaust air has reached the predefined temperature. Then, the active coating suspension is sprayed onto the moving tablet bed in the coater until the predefined end criterion has been reached. Thereafter the tablets are polished in the drum at a drum speed of 12-20 rpm and under unchanged air flow without any further heating of the inlet air for at least further 10 minutes and until the exhaust air temperature has reached 35° C. whatever is longer.

Prior to the coating process, at various times during the coating process and immediately after the coating process, samples of the tablets are taken and investigated in order to monitor the coating process.

A series of process development batches have been manufactured in lab scale starting from cores comprising 33 mg nifedipine according to example 2 by varying drum load, drum speed, spray rate, and spraying time. All batches were investigated for increase in weight and content uniformity of candesartan cilexetil (mean and RSD of 20 individual tablets).

The following process conditions were investigated and resulted in the respective film mass (mean) and candesartan cilexetil content (mean and RSD, n=20). Calculated spraying losses were approx. 0.5-4.0%.

| example no. | drum load [kg] | drum speed [rpm] | spraying rate [g/min] | spraying time [min] | film mass mean [mg] | content mean [mg] | content RSD [%] |
|---|---|---|---|---|---|---|---|
| 4a | 3 | 16 | 8 | 180 | 40.68 | 16.44 | 6.79 |
| 4b | 4 | 16 | 8 | 240 | 40.70 | 15.59 | 7.16 |
| 4c | 3 | 20 | 8 | 180 | 40.49 | 15.73 | 4.52 |
| 4d | 4 | 20 | 8 | 240 | 39.58 | 16.33 | 4.61 |
| 4e | 3 | 16 | 16 | 90 | 45.82 | 17.67 | 9.85 |
| 4f | 4 | 16 | 16 | 120 | 43.34 | 16.00 | 13.38 |
| 4g | 3 | 20 | 16 | 90 | 39.76 | 15.99 | 6.66 |
| 4h | 4 | 20 | 16 | 120 | 44.12 | 17.09 | 10.77 |
| 4i | 3.5 | 18 | 12 | 145 | 41.12 | 16.72 | 7.30 |
| 4j | 3.5 | 18 | 12 | 145 | 41.66 | 16.40 | 8.76 |
| 4k | 3.5 | 18 | 12 | 145 | 41.34 | 16.75 | 8.46 |

Statistical analysis (ANOVA) demonstrates that the inter-tablet variability is reduced when drum load and spraying rate are decreased (i.e. spraying time is increased) and drum speed is increased. Furthermore, drum load and spraying rate are subject to an interaction. Applying these general statistical finding, the process parameters can be adjusted to achieve the desired results. For example, the results demonstrate that the inter-tablet variability can reproducibly be kept below 5% by selecting a spraying rate of 8 g/min, a drum speed of 20 rpm and a drum load of 3-4 kg, preferably 3 kg. The required spraying time can easily be calculated.

Furthermore, the effect of the number of spray nozzles was investigated. For that purpose, two additional coating runs were performed using the very same conditions that led to the best (4c) and worst (4f) results in term of content RSD with the only difference that a modified spraying arm equipped with 4 ABC nozzles instead of 2 nozzles was used. The following process conditions were investigated and resulted in the respective film mass (mean) and candesartan cilexetil content (mean and RSD, n=30). Calculated spraying losses were approx. 1.5%.

| example no. | drum load [kg] | drum speed [rpm] | spraying rate [g/min] | spraying time [min] | film mass mean [mg] | content mean [mg] | content RSD [%] |
|---|---|---|---|---|---|---|---|
| 4l | 3 | 20 | 8 | 180 | 39.52 | 15.23 | 2.54 |
| 4m | 4 | 16 | 16 | 120 | 41.93 | 15.22 | 4.50 |

Increasing the number of spray nozzles surprisingly improved the content uniformity dramatically as can be seen from the comparison of the respective results for 4c vs. 4l and 4f vs. 4m.

This finding was further confirmed by an additional set of experiments using the modified spraying arm equipped with 4 ABC nozzles instead of 2 nozzles described above. The following process conditions were investigated and resulted in the respective film mass (mean) and candesartan cilexetil content (mean and RSD, n=20). Air flow was 160 $m^3$/h for all experiments except for experiments 4x, 4y and 4z where air flow had been increased to 220 $m^3$/h.

| example no. | drum load [kg] | drum speed [rpm] | spraying rate [g/min] | spraying time [min] | film mass mean* [mg] | content mean [mg] | content RSD [%] |
|---|---|---|---|---|---|---|---|
| 4n | 3 | 16 | 8 | 180 | 41.20 | 16.48 | 3.05 |
| 4m | 4 | 16 | 8 | 240 | 40.78 | 16.31 | 3.42 |
| 4o | 3 | 20 | 8 | 180 | 38.35 | 15.34 | 2.66 |
| 4p | 4 | 20 | 8 | 240 | 38.55 | 15.42 | 2.58 |
| 4q | 3 | 16 | 16 | 90 | 39.45 | 15.78 | 6.43 |
| 4r | 4 | 16 | 16 | 120 | 38.13 | 15.25 | 5.07 |
| 4s | 3 | 20 | 16 | 90 | 41.08 | 16.43 | 4.80 |
| 4t | 4 | 20 | 16 | 125 | 41.33 | 16.53 | 2.28 |
| 4u | 3.5 | 18 | 12 | 140 | 40.75 | 16.30 | 3.05 |
| 4v | 3.5 | 18 | 12 | 140 | 42.13 | 16.85 | 2.86 |
| 4w | 3.5 | 18 | 12 | 145 | 40.88 | 16.35 | 3.54 |
| 4x | 4 | 20 | 24 | 80 | 40.78 | 16.31 | 5.50 |
| 4y | 3 | 20 | 24 | 60 | 40.83 | 16.33 | 4.43 |
| 4z | 4 | 20 | 32 | 60 | 40.98 | 16.39 | 14.15 |

*calculated based on either mass difference before and after coating (4n-w) or content (4x-z)

Statistical analysis (ANOVA) demonstrates that the inter-tablet variability is reduced when spraying rate is decreased (i.e. spraying time is increased) and drum speed is increased.

Example 5

Manufacturing of the Active Coating Layer in a Increased Lab Scale Coater (Ca. 8-10 Kg Drum Load)

Likewise the same coater as used in example 4 can be operated using another coating drum. In that case, the following process conditions apply:
Coater: drum coater BFC 5(10) from L. B. BOHLE Maschinen+Verfahren GmbH, D-59320 Ennigerloh, fitted with the big drum (dimensions: 396 mm diameter, 480 mm overall length, 360 mm cylindrical length) and a spray arm having 2 ABC spray nozzles.
Coater load: 8-10 kg of cores according to Example 2
Drum speed: 15 rpm (revolutions per minute), corresponding to 0.3 m/s peripheral speed Air flow: 235 m³/h
Inlet air temperature: 60° C.
Criterion to start spraying: exhaust air temperature >40° C.
  Spray arm position: 46°, 1 cm
  Spray nozzles diameter: 1.0 mm
  Spray pressure: 1.1 bar
  Forming air pressure: 1.1 bar
  Spraying rate: 24-36 g/min
  Inlet air temperature during spraying: 60° C.
  Exhaust air temperature during spraying: ca. 40-50° C. (dependent on the selected process parameters)
  Criteria to stop spraying step: the spraying is done until either (a) a predefined spraying time is reached or (b) a predefined amount of coating suspension has been used for spraying or (c) until the tablets in the coater have gained a predefined increase in weight, film thickness and/or candesartan cilexetil content.
  Typical total spraying time: ca. 100-200 min
  Polishing at a drum speed of 4-14 rpm and under unchanged air flow without any further heating of the inlet air for at least further 10 minutes and until the exhaust air temperature has reached 35° C. whatever is longer.

Example 6

Manufacturing of the Active Coating Layer in a Pilot Scale Coater

Coater: drum coater BFC 50 from L. B. BOHLE Maschinen+Verfahren GmbH, D-59320 Ennigerloh, fitted with a 50 kg nominal capacity drum (dimensions: 700 mm diameter, 850 mm overall length, 630 mm cylindrical length) and a spray arm having 5 ABC spray nozzles.
Coater load: 133,000-143,000-153,000 of cores comprising 33 mg nifedipine according to Example 2, corresponding to 37-40-43 kg, corresponding to 74%-80%-86% of nominal load.
Drum speed: 12-13-14 rpm (revolutions per minute), corresponding to 0.44-0.47-0.51 m/s peripheral speed
  Air flow: 1000 m³/h
  Inlet air temperature: 60° C.
  Criterion to start spraying: exhaust air temperature >40° C.
  Spray arm position: 50°, 5.5 cm
  Spray nozzles diameter: 1.0 mm
  Spray pressure: 1.7-1.8-1.9 bar
  Forming air pressure: 1.7-1.8-1.9 bar
  Spraying rate: 60-90-120 g/min
  Inlet air temperature during spraying: controlled in such a way that the target exhaust air temperature is met, should however not exceed 60° C., typical values: 48-55° C.
Exhaust air temperature during spraying: target 42° C.
  Criteria to stop spraying step: the spraying is done until either (a) a predefined spraying time is reached or (b) a predefined amount of coating suspension has been used for spraying or (c) until the tablets in the coater have gained a predefined increase in weight, film thickness and/or candesartan cilexetil content.
  Typical total spraying time: ca. 150-300 min
  Typical yield of spraying: 98.0-99.5%
  A weighed amount of tablet cores is introduced into the coater and pre-warmed until exhaust air has reached the predefined temperature. Then, the active coating suspension is sprayed onto the moving tablet bed in the coater until the predefined end criterion has been reached. Thereafter the tablets are polished in the drum at a drum speed of 4-14 rpm and under unchanged air flow without any further heating of the inlet air for at least further 10 minutes and until the exhaust air temperature has reached 35° C. whatever is longer.

Prior to the coating process, at various times during the coating process and immediately after the coating process, samples of the tablets are taken and investigated in order to monitor the coating process.

A series of process development batches have been manufactured in lab scale starting from cores comprising 33 mg nifedipine according to example 2 by varying drum load, drum speed, spraying pressure (same values also used for forming air pressure), spraying rate, and spraying time. The following process conditions were investigated:

| example no. | drum load [tablets] | drum speed [rpm] | spraying pressure [bar] | spraying rate [g/min] | spraying time [min] |
|---|---|---|---|---|---|
| 6a | 143000 | 13 | 1.8 | 90 | 225 |
| 6b | 133000 | 12 | 1.7 | 120 | 150 |
| 6c | 133000 | 12 | 1.9 | 120 | 300 |
| 6d | 133000 | 12 | 1.9 | 60 | 150 |
| 6e | 153000 | 14 | 1.9 | 120 | 300 |
| 6f | 133000 | 14 | 1.9 | 120 | 150 |
| 6g | 133000 | 14 | 1.7 | 120 | 300 |
| 6h | 133000 | 14 | 1.7 | 60 | 150 |
| 6i | 144507 | 13 | 1.8 | 90 | 225 |
| 6j | 153000 | 12 | 1.9 | 60 | 300 |
| 6k | 153000 | 12 | 1.7 | 60 | 150 |
| 6l | 153000 | 12 | 1.7 | 120 | 300 |
| 6m | 153000 | 12 | 1.9 | 120 | 150 |
| 6n | 153000 | 14 | 1.7 | 60 | 300 |
| 6o | 153000 | 14 | 1.9 | 60 | 150 |
| 6p | 133000 | 12 | 1.7 | 60 | 300 |
| 6q | 153000 | 14 | 1.7 | 120 | 150 |
| 6r | 133000 | 14 | 1.9 | 60 | 300 |
| 6s | 143000 | 13 | 1.8 | 90 | 225 |

The following results were obtained for film thickness as determined via Terahertz Pulsed Imaging (mean red tablet side, mean yellow tablet side, average of both sides mean and RSD, n=10, method described in example 8 in more detail), and candesartan cilexetil content as determined via HPLC (mean and RSD, n=30). Calculated spraying losses were approx. 0.5-2.5%.

| example no. | film thickness red side mean [μm] | film thickness yellow side mean [μm] | film thickness average mean [μm] | film thickness average RSD [%] | content mean [mg] | content RSD [%] |
|---|---|---|---|---|---|---|
| 6a | 196.7 | 198.0 | 197.4 | 5.62 | 16.12 | 5.33 |
| 6b | 189.9 | 199.0 | 194.4 | 7.40 | 16.13 | 6.45 |
| 6c | 355.2 | 358.5 | 356.9 | 3.85 | 32.02 | 5.48 |
| 6d | 97.5 | 96.6 | 97.1 | 4.15 | 6.82 | 5.30 |
| 6e | 303.9 | 311.1 | 307.5 | 5.91 | 27.26 | 4.26 |
| 6f | 189.9 | 188.7 | 189.3 | 4.67 | 16.18 | 6.09 |
| 6g | 356.0 | 353.3 | 354.7 | 4.27 | 31.38 | 5.43 |
| 6h | 89.6 | 94.0 | 91.8 | 5.70 | 6.68 | 3.97 |
| 6i | 189.7 | 190.3 | 190.0 | 6.10 | 16.39 | 5.62 |
| 6j | 165.3 | 170.7 | 168.0 | 5.75 | 13.36 | 4.11 |
| 6k | 89.2 | 90.9 | 90.0 | 6.99 | 6.58 | 5.82 |
| 6l | 243.8 | 253.9 | 248.9 | 9.50 | 27.81 | 8.17 |
| 6m | 113.0 | 116.4 | 116.9 | 9.49 | 13.65 | 11.12 |
| 6n | 163.9 | 161.9 | 162.9 | 3.39 | 13.23 | 2.72 |
| 6o | 93.3 | 96.9 | 95.1 | 4.01 | 6.72 | 4.66 |
| 6p | 186.3 | 185.4 | 185.9 | 5.96 | 14.76 | 4.27 |
| 6q | 174.1 | 175.6 | 174.9 | 6.04 | 14.30 | 6.89 |
| 6r | 189.8 | 194.3 | 192.1 | 3.35 | 14.96 | 3.17 |
| 6s | 195.1 | 204.4 | 199.7 | 5.02 | 15.82 | 4.67 |

The inter-tablet variability results determined by two different methods (TPI film thickness and HPLC assay) are in good agreement to each other (linear correlation was found with a $R^2$ of 0.85). Statistical analysis (ANOVA) demonstrates that the inter-tablet variability is reduced when spraying rate is decreased and drum speed and spraying time are increased. Furthermore, in the case of low drum speed, inter-tablet variability is slightly reduced when drum load is decreased. Spraying pressure does not significantly influence the inter-tablet variability. Applying these general statistical finding, the process parameters can be adjusted to achieve the desired results. For example, in the selected batch scale and equipment, the following process parameters can be used to minimize the inter-tablet variability of active ingredient assay and simultaneously maximize the batch size:

| example no. | dose strength [mg] | drum load [kg] | drum speed [rpm] | spraying pressure [bar] | spraying rate [g/min] | spraying time [min] | content RSD point prediction (95% PI) [%] |
|---|---|---|---|---|---|---|---|
| 6t | 8 | 43 | 14 | 1.7 | 60 | 180 | 3.7 (2.5-4.8) |
| 6u | 16 | 43 | 14 | 1.9 | 73.5 | 290 | 2.5 (1.4-3.6) |

Most importantly, selecting appropriate process parameters according to the ANOVA model results, the relative standard deviation of the assay can be limited to values below 5% for the 8 mg candesartan cilexetil dose strength and even below 4% for the 16 mg dose strength applied as active film coating onto cores comprising 33 mg nifedipine.

Besides the inter-tablet variability, the intra-tablet film thickness variability was also determined via Terahertz Pulsed Imaging (RSD of all film thickness measurements on the red side of one tablet, RSD of all film thickness measurements on the yellow side of one tablet, thickness ratio red side/yellow side). In addition, the thickness ratio tablet face (mean of yellow and red site): center (central band) was calculated. The following table lists the mean values calculated from the individual RSD or ratio values of n=10 tablets:

| example no. | Intratablet thickness layer variability (red tablet side) RSD [%] | Intratablet thickness layer variability (yellow tablet side) RSD [%] | Thickness layer ratio red:yellow | Thickness layer ratio face:center |
|---|---|---|---|---|
| 6a | 3.98 | 3.54 | 0.994 | 1.103 |
| 6b | 4.32 | 3.76 | 0.954 | 1.083 |
| 6c | 3.07 | 3.46 | 0.991 | 1.087 |
| 6d | 4.96 | 5.12 | 1.009 | 1.195 |
| 6e | 2.97 | 2.72 | 0.977 | 1.151 |
| 6f | 3.44 | 3.46 | 1.006 | 1.083 |
| 6g | 2.45 | 2.58 | 1.008 | 1.072 |
| 6h | 5.27 | 5.14 | 0.954 | 1.196 |
| 6i | 3.66 | 3.83 | 0.997 | 1.104 |
| 6j | 4.16 | 4.22 | 0.969 | 1.196 |
| 6k | 6.13 | 5.52 | 0.982 | 1.182 |
| 6l | 3.56 | 3.20 | 0.960 | 1.063 |
| 6m | 6.48 | 6.12 | 0.971 | 1.127 |
| 6n | 3.61 | 3.77 | 1.012 | 1.106 |
| 6o | 5.69 | 5.67 | 0.963 | 1.134 |
| 6p | 4.72 | 4.76 | 1.005 | 1.132 |
| 6q | 5.22 | 5.07 | 0.992 | 1.106 |
| 6r | 4.23 | 4.10 | 0.977 | 1.143 |
| 6s | 3.94 | 3.86 | 0.955 | 1.111 |

Statistical analysis (ANOVA) demonstrates that the intra-tablet variability is reduced when drum load is decreased and drum speed, spraying rate and spraying time are increased.

Example 7

Manufacturing of the Active Coating Layer in a Commercial Scale Coater

Coater: drum coater BFC 400 from L. B. BOHLE Maschinen+Verfahren GmbH, D-59320 Ennigerloh (dimensions: 1430 mm diameter, 2200 mm overall length, 1610 mm cylindrical length), fitted with a spray arm having ABC 4 spray nozzles.

Coater load: 240-250-260 kg of cores according to Example 2, corresponding to 60%-62.5%-65% of nominal loadDrum speed: 9 rpm (revolutions per minute), corresponding to 0.675 m/s peripheral speed Air flow: 2500-3000-4000 m$^3$/h Inlet air temperature: 60° C.

Criterion to start spraying: exhaust air temperature >40° C.

Spray arm position: 55°

Gun-bed distance: ca. 20-22 cm

Spray nozzles diameter: 1.2 mm

Spray pressure: 3.0 bar

Forming air pressure: 2.5 bar

Spraying rate: 160-360 g/min

Inlet air temperature during spraying: controlled in such a way that the target exhaust air temperature is met, should however not exceed 60° C., typical values: 48-55° C.

Exhaust air temperature during spraying: target 42° C.

Criteria to stop spraying step: the spraying is done until either (a) a predefined spraying time is reached or (b) a predefined amount of coating suspension has been used for spraying or (c) until the tablets in the coater have gained a predefined increase in weight, film thickness and/or candesartan cilexetil content.

Typical total spraying time: ca. 4-9 hours

Typical yield of spraying: 98.0-99.5%

A weighed amount of tablet cores is introduced into the coater and pre-warmed until exhaust air has reached the predefined temperature. Then, the active coating suspension is sprayed onto the moving tablet bed in the coater until the predefined end criterion has been reached. Thereafter the tablets are polished in the drum at a drum speed of 4-9 rpm and under unchanged air flow without any further heating of the inlet air for at least further 10 minutes and until the exhaust air temperature has reached 35° C. whatever is longer.

Prior to the coating process, at various times during the coating process and immediately after the coating process, samples of the tablets are taken and investigated in order to monitor the coating process.

A series of scale-up batches have been manufactured in commercial scale starting from cores comprising either 33 mg or 66 mg nifedipine according to example 2 by varying drum load, air flow, spray rate, and spraying time. The spraying was stopped after a predefined amount of coating suspension had been applied. All batches were investigated for increase in weight (apparent film mass) and content uniformity of candesartan cilexetil (mean and RSD of 30 individual tablets).

The following process conditions were investigated and resulted in the respective film mass (mean) and candesartan cilexetil content (mean and RSD). Calculated spraying losses were approx. 0.5-3.0%.

| example no. | dose strength N + CC* [mg] | drum load [kg] | air flow [m³/h] | spraying rate [g/min] | spraying time [min] | film mass mean [mg] | content mean [%] | content RSD [%] |
|---|---|---|---|---|---|---|---|---|
| 7a | 30 + 8 | 260 | 2900 | 360 | 172 | 22.2 | 100.5 | 8.3 |
| 7b | 30 + 8 | 240 | 2900 | 240 | 248 | 21.6 | 101.7 | 6.6 |
| 7c | 60 + 16 | 260 | 2900 | 210 | 292 | 44.0 | 103.8 | 6.3 |
| 7d | 30 + 8 | 250 | 2900 | 160 | 368 | 20.3 | 100.3 | 4.9 |
| 7e | 60 + 16 | 240 | 2900 | 180 | 373 | 43.1 | 103.8 | 4.9 |
| 7f | 30 + 16 | 250 | 2900 | 360 | 345 | 44.5 | 101.9 | 4.0 |
| 7g | 60 + 32 | 260 | 2900 | 300 | 437 | 84.5 | 101.2 | 5.5 |
| 7h | 60 + 32 | 250 | 2900 | 240 | 528 | 82.2 | 100.1 | 4.8 |
| 7i | 30 + 16 | 250 | 2900 | 240 | 522 | 42.2 | 102.2 | 4.3 |

*N: nifedipine (nominal content); CC: candesartan cilexetil

These results are also depicted in FIG. 1 together with additional content uniformity measurements performed on in-process control samples taken during the manufacture of these batches. The results demonstrate that the inter-tablet variability can reproducibly be kept below 6% by selecting a spraying time of at least ca. 6 hours. The required spraying rate can easily be calculated. The inter-tablet variability can furthermore reproducibly controlled below 5% by selecting a spraying time dependent on the film thickness to applied. For example, the following process conditions can be applied to the selected equipment in order reproducibly manufacture batches with an inter-tablet variability (RSD of candesartan cilexetil content) below 5%.

| example no. | Dose strength N + CC* [mg] | drum load [kg] | air flow [m³/h] | spraying rate [g/min] | spraying time [min] |
|---|---|---|---|---|---|
| 7j | 30 + 8 | 260 | 2800 | 170 | 375 |
| 7k | 30 + 16 | 260 | 3400 | 300 | 425 |
| 7l | 60 + 16 | 260 | 2800 | 170 | 390 |
| 7m | 60 + 32 | 260 | 3400 | 300 | 450 |

*N: nifedipine (nominal content); CC: candesartan cilexetil

These process parameters have been experimentally been confirmed by the following set of experiments:

| example no. | dose strength N + CC* [mg] | drum load [kg] | air flow [m³/h] | spraying rate [g/min] | spraying time [min] | film mass mean [mg] | content mean [%] | content RSD [%] |
|---|---|---|---|---|---|---|---|---|
| 7jj | 30 + 8 | 260 | 2800 | 170 | 370 | 20.03 | 97.6 | 4.0 |
| 7kk | 30 + 16 | 260 | 3400 | 280 | 425 | 41.10 | 97.9 | 2.3 |
| 7ll | 60 + 16 | 257 | 2800 | 170 | 377 | 41.21 | 101.3 | 3.8 |
| 7mm | 60 + 32 | 260 | 3400 | 300 | 423 | 82.86 | 100.2 | 3.7 |

*N: nifedipine (nominal content); CC: candesartan cilexetil

Example 8

Off-Line Process Monitoring Using Terahertz Pulsed Imaging

Tablets were analysed by Terahertz Pulsed Imaging (TPI) using a TPI imaga 2000 system (TeraView Ltd., Cambridge, UK). A measurement in full scan mode consisted of scanning both faces of the tablet as well as the centre band with a spot size of 200×200 µm and a penetration depth of 2 mm in air. Measurements of in-process-control samples used a limited circular sampling area on the surface of each tablet face (e.g. 4 mm radius) in order to reduce data acquisition time. No data was acquired from the centre band in these samples.

Coating thickness analysis was performed using TPIView software version 3.0.3 (TeraView Ltd., Cambridge, UK). The refractive index was set to n=1:53, which is default value in the software. Matlab version R2009a (Mathworks, Ismaning, Germany) was used to extract the average value of the coating thickness and standard deviation for each tablet side separately. For the data analysis all pixels on the tablet edges as well as the pixels in the region of the laser drilled hole were excluded to avoid scattering artefacts. The region of interest was defined by a torus of 1.5 mm inner radius and 3 mm outer radius with reference to the centre of the tablet face, including approximately 500 data points per tablet face.

Figure 2:
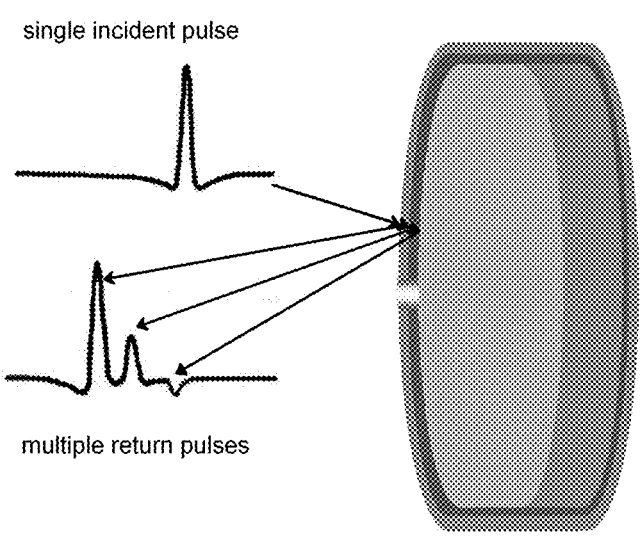
FIG. 2 is a depiction of typical TPI signals at an individual sampling point, illustrating a single incident terahertz pulse and multiple return pulses created by interface reflections of the radiation.
Figure 3:
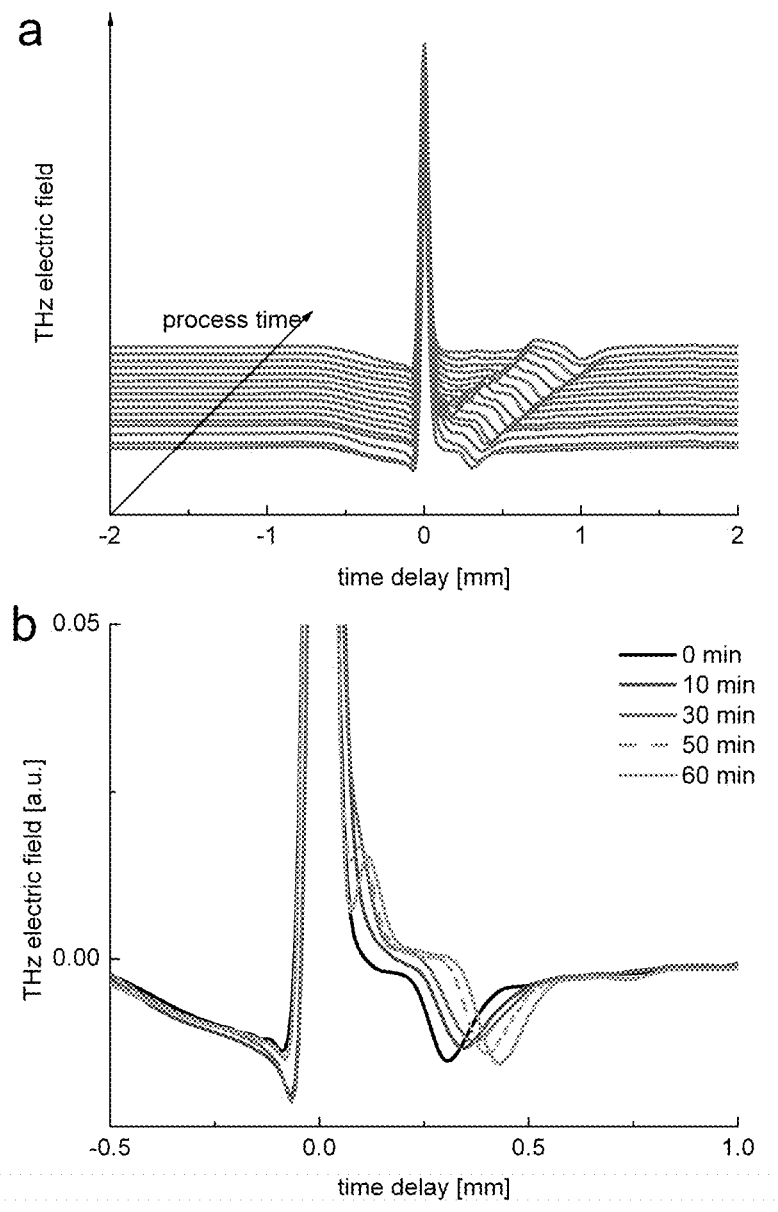
FIG. 3 illustrates typical changes to the TPI signals during the coating process.

Typical TPI signals on an individual sampling point are shown in FIG. 2. Depicted is the single incident terahertz pulse and the multiple return pulses created by the interface reflections of the radiation. Typical changes to the TPI signals during the coating process are shown in FIG. 3.

Figure 4:
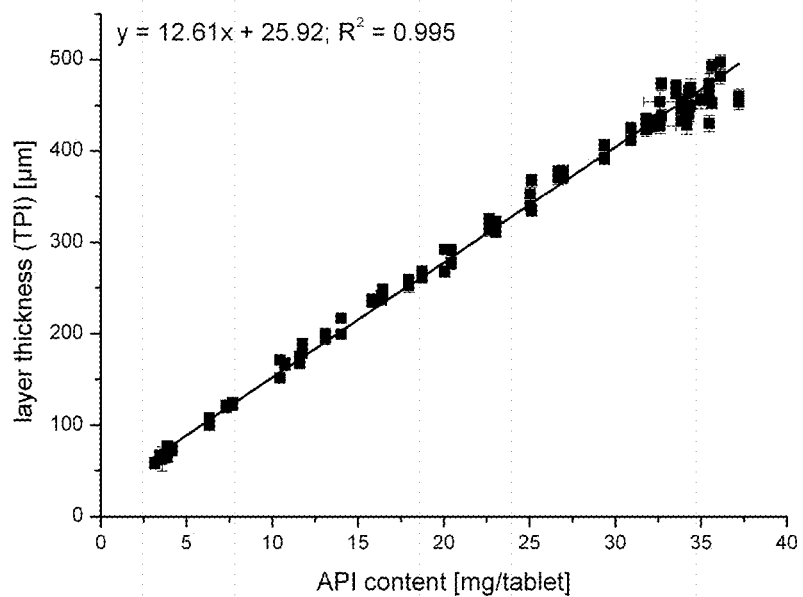
FIG. 4 is a plot of the mean film thickness of the active coating on both sides of in-process control samples of selected tablet batches produced as described in example 4, as determined via off-line Terahertz Pulsed Imaging (TPI)
Figure 5:
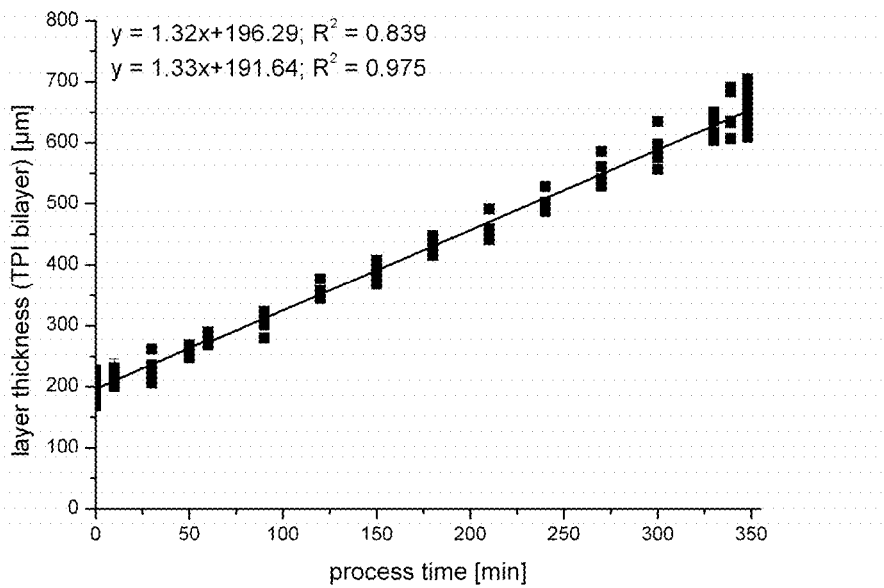
FIG. 5 provides an example of results of an evaluation of the sum of organic and active coating thickness over time.

For in-process control samples of selected tablet batches according to example 4, the mean film thickness of the active coating on both tablet sides determined via off-line Terahertz Pulsed Imaging were compared to the respective assay results as determined via HPLC as displayed in FIG. 4. The minimum film thickness that can be detected is approximately 60-70 µm. In order to monitor the process even earlier, the sum of organic and active coating thickness can be evaluated over process time as displayed in FIG. 5.

Figure 6:
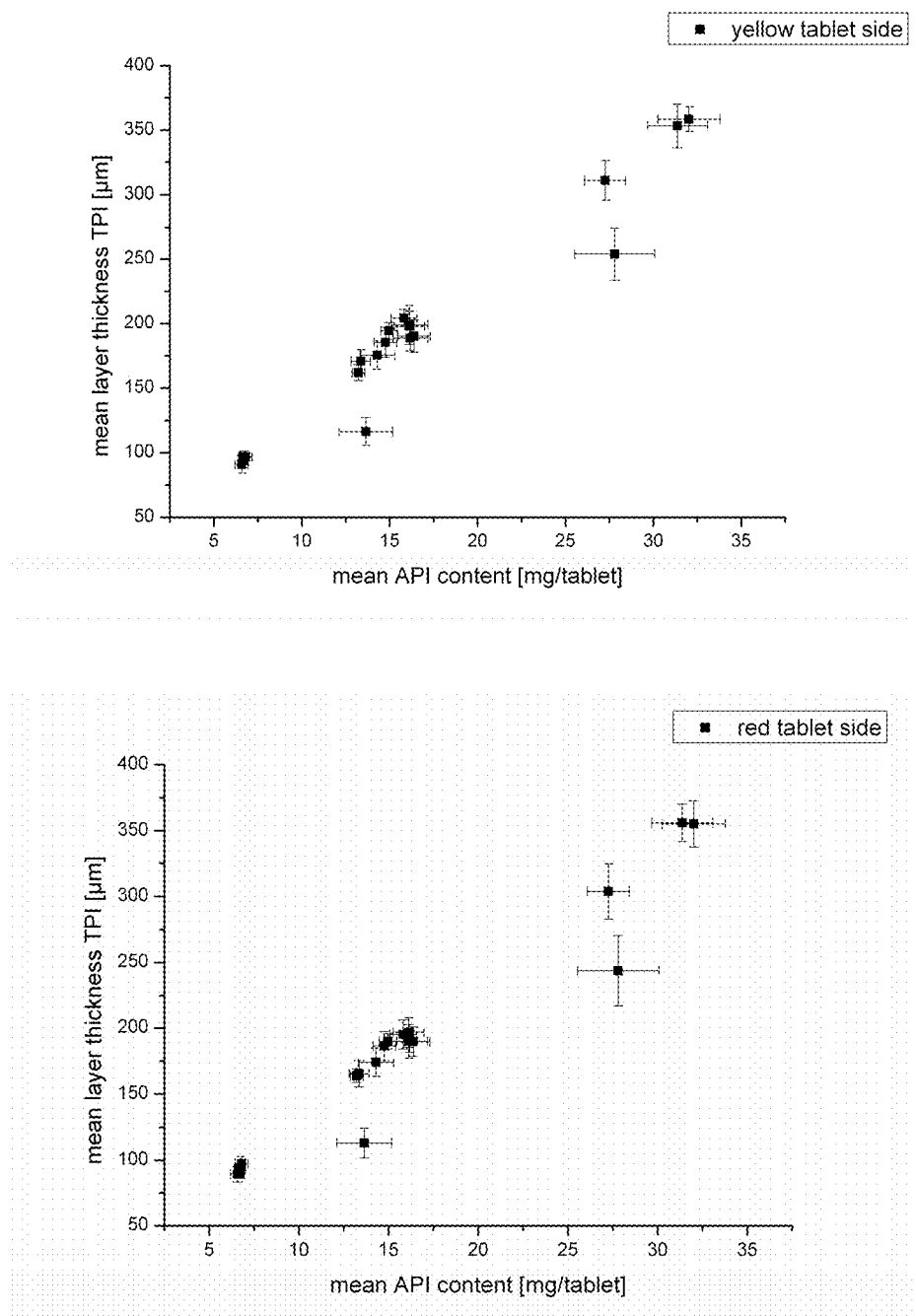
FIG. 6 is a plot of mean layer thickness TPI vs mean API content of the red and yellow sides of tablets produced according to example 6.

For tablets according to example 6, the mean film thickness on both tablet sides determined via off-line Terahertz Pulsed Imaging were compared to the respective assay results as determined via HPLC as displayed in FIG. 6 (n=10 tablets per batch).

In general, the film thickness correlates well with the content of active ingredient. However, two of the batches investigated showed deviating Terahertz results as shown in FIG. 6. Without wishing to be limited to a specific theory, this deviation might be attributed to slight differences in the structure of the film that significantly changes Terahertz results. Moreover, the correlation exhibits relatively high variability. For these two reasons, Terahertz Pulsed Imaging is at present rated not sufficiently predictive for in-line and/or at-line process monitoring for this specific active coating process.

Example 9

At-line Process Monitoring Using NIR Spectroscopy

For at-line NIR measurements, a FT-NIR-spectrometer type MPA (Bruker Optik GmbH, Ettlingen, Germany) was used. At-line measurements of individual tablets were performed in transmission mode (resolution 8 cm$^{-1}$, 64 scans) while the tablets were placed in suitable tablet holders the osmotic layer positioned next the NIR light source.

For the model calibration, tablets were collected at three different stages of the coating processes during selected coating runs as described in example 6 and 7 covering candesartan cilexetil amounts from 1 to 36 mg. The tablets (n=30 per sampling point) were measured by NIR spectroscopy in a spectral range from ca. 6000 cm$^{-1}$ to 12000 cm$^{-1}$. Then, multivariate model (PLS) was built up with this data set. When NIR measurements in transmission mode are performed on tablets containing 66 mg nifedipine and having an overall thickness of ca. 7 mm, the overall absorption was expectedly higher as compared to measurements on tablets containing 33 mg nifedipine and having an overall thickness of ca. 5 mm. For that reason, different spectral ranges had also to be selected in these two cases:

|  | tablets containing 33 mg nifedipine | tablets containing 66 mg nifedipine |
| --- | --- | --- |
| spectral ranges for evaluation | 9041.1-8134.7 cm$^{-1}$<br>6618.8-6341.1 cm$^{-1}$ | 9380.5-8385.4 cm$^{-1}$<br>8030.5-7251.4 cm$^{-1}$ |

Spectral data were appropriately centered and preprocessed (first derivative and linear subtraction). As reference analytical method, HPLC analysis was applied to the same tablets, in order to obtain the amount of coated API. The PLS calibration models were evaluated by cross-validation. The resulting PLS models typically exhibited 5 to 6 principal components and were able to predict the candesartan cilexetil amounts at the end of the coating runs with an accuracy deviation of 1-4% depending on the selected data sets for cross-validation. Mean deviation was 1.0% for tablets containing 33 mg nifedipine in the tablet core and 1.4% for tablets containing 66 mg nifedipine.

Example 10

At-line Process Monitoring Using Raman Spectroscopy

For the Raman measurements a RamanRXN2 analyzer of Kaiser Optical Systems (Ann Arbor, USA) with a laser wavelength of 785 nm was used. The spectrometer was equipped with a non-contact optic sampling device (PhAT probe). The excitation light which is passing through the optical fibers is collimated by a lens and imaged onto the sample to form a circular illumination area of 6 mm diameter (area: 28.3 mm$^2$). This relatively large spot size as compared to traditional confocal Raman probes improves the reliability and reproducibility of Raman measurements. To accomplish this, the focal length of the sample optic is greater than the focal length of the excitation optic.

Data collection and all the calculations including spectral preprocessing, intensity normalization and partial least squares (PLS) regression, were done using icRaman® data collection software package (Kaiser Optical Systems, Ann Arbor, USA), SIMCA-P®+12.0.1 (Umetrics, Umea, Sweden), the Matlab® software package (version 6.5, The MathWorks, Inc., Natick, Mass., USA), OriginPro 8G® (OriginLab Corporation, Northhampton, Mass., USA) and Excel® (version 2007, Microsoft Corporation).

For the model calibration, tablets were collected at different stages of the coating process (e.g. every 30 minutes) from the coater during selected coating runs as described in example 4 covering candesartan cilexetil amounts from 0 to 33 mg. These tablets (in total n=120) were measured by Raman spectroscopy with a scanning time of 30 seconds for the API-layer or 120 seconds for the osmotic layer, respectively, for each tablet. Then, multivariate model (PLS) was built up with this data set. As reference analytical method, HPLC analysis was applied to the same tablets, in order to obtain the amount of coated API. An extra set of validation samples (in total n=120) was collected during another coating run using the same process and sampling conditions for model validation. The PLS calibration models were evaluated by cross-validation. The optimum latent variable number was selected with respect to the lowest root mean square error of calibration (RMSEC). The most appropriate PLS models were selected from their predictive ability based on the root mean square error of prediction (RMSEP).

The best calibration model was obtained using Standard Normal Variate (SNV) preprocessed spectra in the spectral region from 1540 cm$^{-1}$ to 1750 cm$^{-1}$ and two principal components. The SNV transformation is applied to each individual spectrum in isolation and without any reference to the sample set. This transformation first centers the spectral values by subtracting the mean of the individual spectrum from each value. These centered values are then scaled by the standard deviation calculated from the individual spectrum values. The SNV transformation also resulted in spectra that were independent of product temperature.

Figure 7:
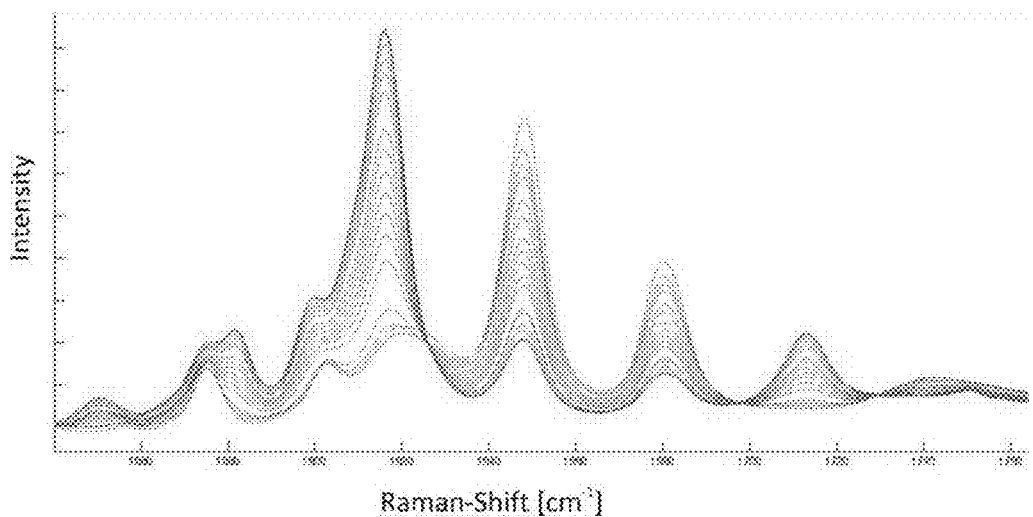
FIG. 7 is Raman spectra obtained at different stages of the coating process of example 12.
Figure 8:
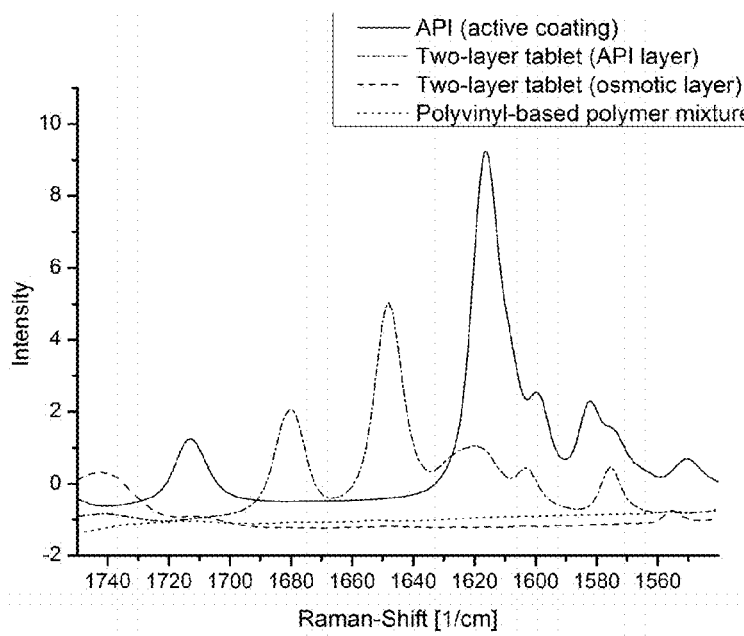
FIG. 8 illustrates the contribution of candesartan cilexetil, the coating material and both layers of the bi-layer tablet to the Raman spectra in tablets produced as described in example 12.
Figure 9:
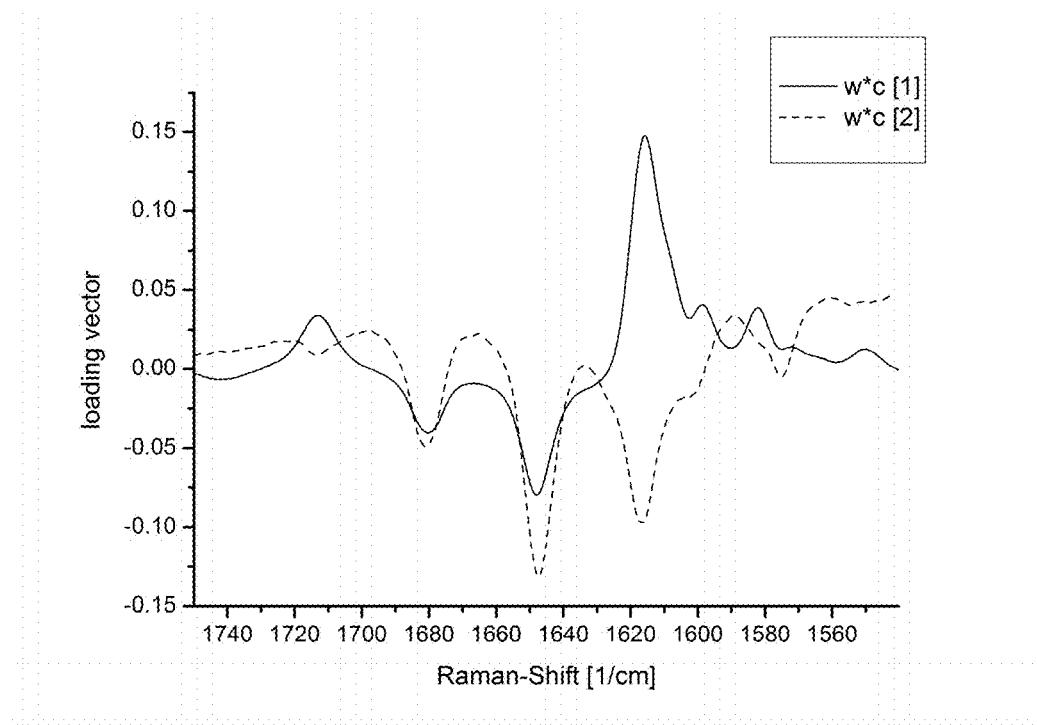
FIG. 9 is a loading plot for the two principal components of the Raman Signals of tablets produced as described in example 12.

Spectra obtained at different stages of coating process according to example 12 are shown in FIG. 7 (spectral range from 1540 cm$^{-1}$ to 1750 cm$^{-1}$). The intensity of the peaks at 1715 cm$^{-1}$ and 1617 cm$^{-1}$ increases as a function of coating time and can be assigned to the candesartan cilexetil in the coating layer. The peak at 1715 cm$^{-1}$ originates from C=O carbonate ester bonds and the peak at 1617 cm$^{-1}$ attributes to a C=C benzene vibration stretch. The contribution of candesartan cilexetil, the coating material and both layers of the bi-layer tablet core are shown in FIG. 8. The loading plots for the two principal components are shown in FIG. 9. In the loading plot of the first principal component, which explains 99% of the variance, several spectral features can be recognized. These features can be assigned to the increasing candesartan cilexetil amount coated onto the tablet cores (1617 cm$^{-1}$ and 1715 cm$^{-1}$) and the decrease in signal intensity of the tablet's nifedipine layer (1648 cm$^{-1}$ and 1680 cm$^{-1}$) due to the increase of coating thickness. The second principal component shows decrease in signal intensity both of candesartan cilexetil and nifedipine due to overall attenuation of the signal intensity with increasing coating film thickness.

The predictions of the API amount applied to the tablets gave a RMSEP of 1.187 mg. At the end of the coating run, the multivariate model predicted the amount of candesartan cilexetil with an accuracy deviation of 4.5%.

Example 11

In-line Process Monitoring Using NIR Spectroscopy

For in-line NIR measurements, a FT-NIR-spectrometer type Matrix-F (Bruker Optik GmbH, Ettlingen, Germany) was used. The spectrometer was equipped with an Hellma type 668.008 (materials: 1.4435, sapphire, Kalrez) optic sampling device (in-line probe). In-line NIR measurements were performed in a commercial scale coater (BFC 400, according to example 7). For that purpose, the probe was mounted inside the coater in a way that it could be immersed into the moving tablet (immersion depth: 7 cm) bed during the coating process.

In-line measurements were performed in reflection mode (resolution 8 cm$^{-1}$, 256 scans, measurement time 2.5 minutes). For the model calibration, tablets were collected at several stages of the coating process from the coater during these coating runs. At the point of sampling the in-line measured NIR spectra were recorded with an exposure time of 120 seconds. (For selected coating runs the exposure time was reduced to 30 seconds which resulted in doubling of the scattering noise.) To build up multivariate calibration models, the in-line NIR spectra obtained during the coating run were correlated with the averaged amount of coated API of n=30 tablets for each of the coating levels that was obtained by HPLC analysis after the coating run had been finished. For cross-validation, these models were applied to in-line measured NIR spectra of another coating run. Then, the amount of coating, which was predicted by the model, was compared with measurements using HPLC analysis.

The following spectral ranges were used for evaluation:

|  | tablets containing 33 mg nifedipine | tablets containing 66 mg nifedipine |
| --- | --- | --- |
| spectral ranges for evaluation | 8789.8-7898.9 cm$^{-1}$ 6703.3-6101.6 cm$^{-1}$ | 8789.8-7625.1 cm$^{-1}$ 7251.0-7116.0 cm$^{-1}$ 6132.0-5434.4 cm$^{-1}$ |

Spectral data were appropriately centered and preprocessed (first derivative and MSC). The resulting PLS models typically exhibited 2 to 3 principal components and were able to predict the candesartan cilexetil amounts at the end of the coating runs with an mean accuracy deviation of 2.1% for tablets containing 33 mg nifedipine in the tablet core and 0.8% for tablets containing 66 mg nifedipine.

Example 12

In-line Process Monitoring Using Raman Spectroscopy

For in-line Raman measurements, the same equipment and software as described in example 10 were used. In-line Raman measurements were performed, both in a lab scale coater (BFC 5, according to example 4) and a commercial scale coater (BFC 400, according to example 7).

For measurements in the BFC5 lab scale coater, the PhAT probe was attached outside at the front of the coater to collect Raman spectra during the coating process with a working distance of 22 cm.

To protect the probe from dust, compressed air was blown through a stainless steel tube, which was attached in front of the probe.

For the model calibration, tablets were collected at 12 different stages of the coating process from the coater during selected coating runs as described in example 4 covering candesartan cilexetil amounts from 0 to 33 mg. At the point of sampling the in-line measured Raman spectra were recorded with an exposure time of 60 seconds. To build up multivariate calibration models, these 12 in-line Raman spectra obtained during the coating run were correlated with the averaged amount of coated API of n=10 tablets for each of the 12 coating levels that was obtained by HPLC analysis after the coating run had been finished. For cross-validation, these models were applied to in-line measured Raman spectra of another coating run. Then, the amount of coating, which was predicted by the model, was compared with measurements using HPLC analysis. Preprocessing and modeling was performed in the same way as described in example 10.

The predictions of the API amount applied to the tablets surprisingly gave a RMSEP of 0.658 mg indicating an much smaller error of the model as compared to at-line measurement. At the end of the coating run, the multivariate model predicted the amount of candesartan cilexetil with an accuracy deviation of 0.8%.

For measurements in the BFC400 commercial scale coater, the PhAT probe was attached inside the coater to the spraying arm midway between two spray nozzles to collect Raman spectra during the coating process with a working distance of 22 cm. To protect the probe from dust, compressed air was blown through a stainless steel tube, which was attached in front of the probe. Coating runs according to examples 7b, 7c, 7d, 7f, 7g, 7h, and 7i were monitored by Raman spectroscopy.

For the model calibration, tablets were collected at several stages of the coating process from the coater during these coating runs. At the point of sampling the in-line measured Raman spectra were recorded with an exposure time of 60 seconds. The multivariate calibration models were established in the same way as for the at-line monitoring in the lab-scale.

Figure 10:
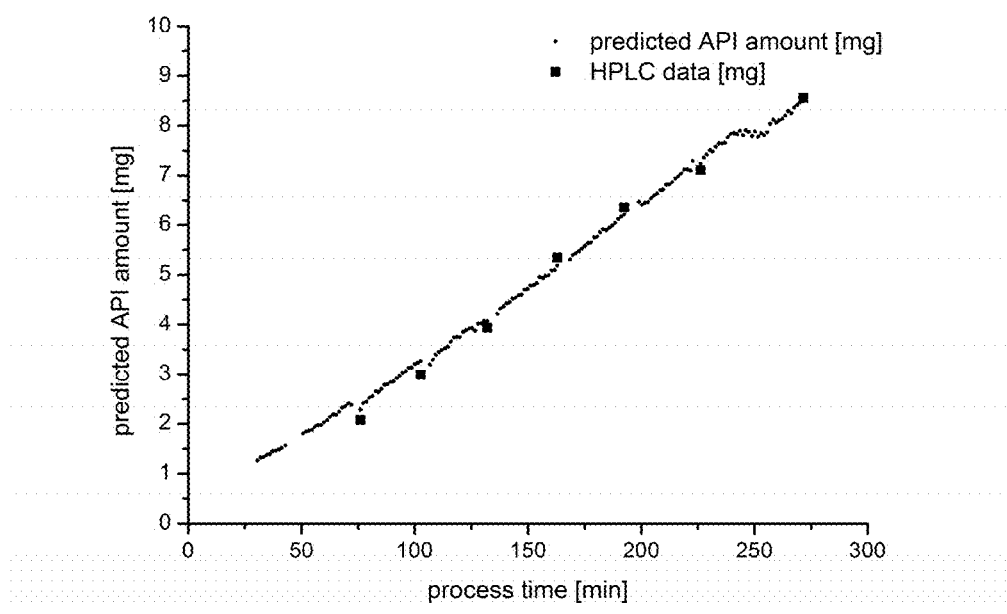
FIG. 10 is a comparison of candesartan cilexetil amounts predicted using a multivariate model obtained from in-line measurements in the lab-scale coater according to the process of example 4 with actual HPLC data of tablets during active coating in a commercial scale coater according to the process of example 7b.
Figure 11:
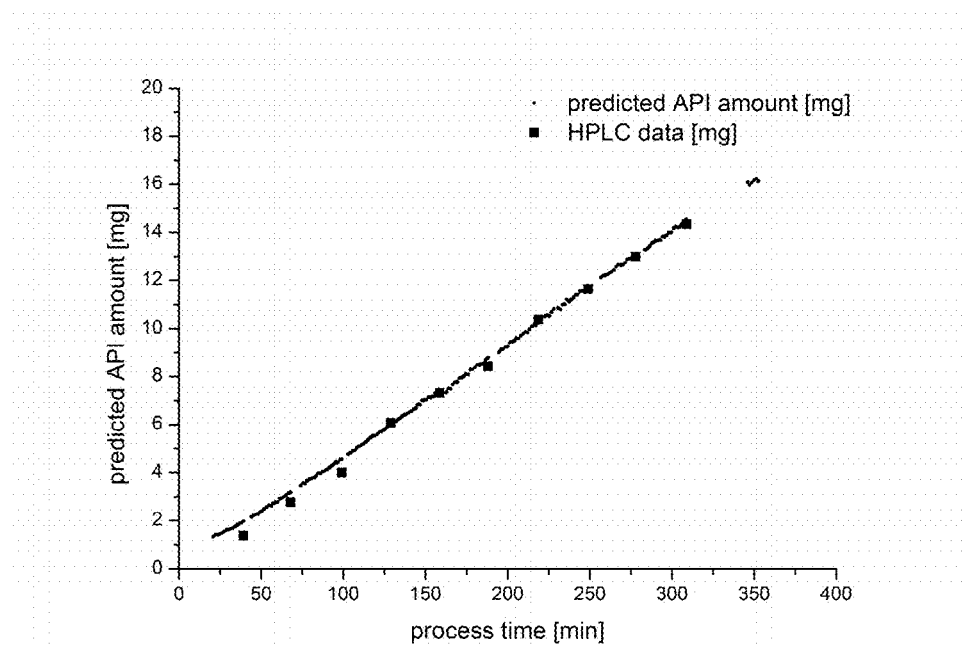
FIG. 11 is a comparison of candesartan cilexetil amounts predicted using a multivariate model obtained from in-line measurements in the lab-scale coater according to the process of example 4 with actual HPLC data of tablets during active coating in a commercial scale coater according to the process of example 7f.
Figure 12:
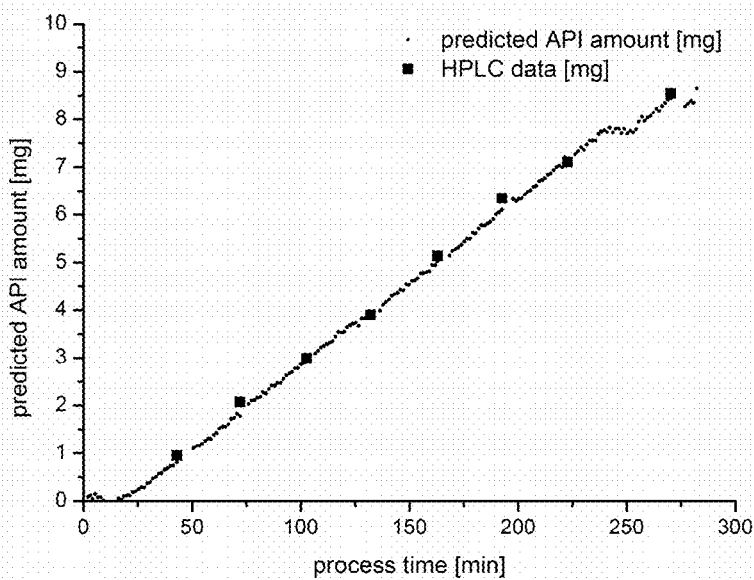
FIG. 12 is a comparison of candesartan cilexetil amounts predicted using a multivariate model obtained from in-line measurements in the commercial scale coater according to the process of example 7 with actual HPLC data of tablets during active coating in a commercial scale coater according to the process of example 7b.
Figure 13:
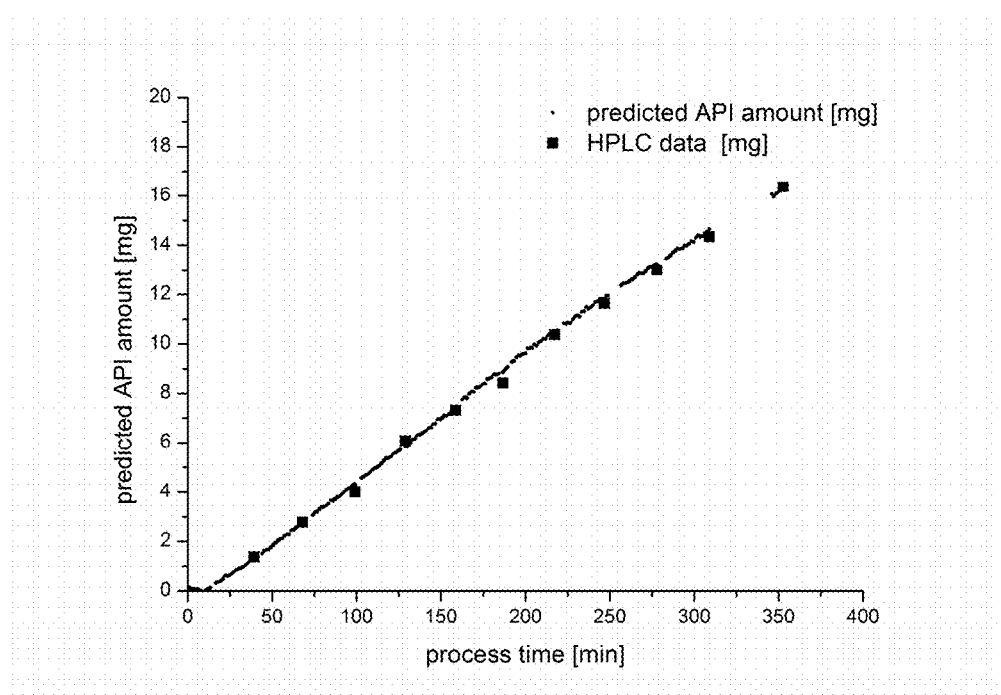
FIG. 13 is a comparison of candesartan cilexetil amounts predicted using a multivariate model obtained from in-line measurements in the commercial scale coater according to the process of example 7 with actual HPLC data of tablets during active coating in a commercial scale coater according to the process of example 7f.

Surprisingly, the multivariate model obtained from in-line measurements in the lab-scale coater could directly be used to predict the amount of candesartan cilexetil of tablets during active coating in the commercial scale coater as can be seen from FIG. 10 and FIG. 11, representing examples 7b and 7f, resp. Further improvement of the prediction was achieved by using the Raman spectra obtained during coating runs in the commercial scale coater according to examples 7b, 7c, 7d, 7f, 7g, 7h, and 7i and predicting candesartan cilexetil amounts of another batches of the same series as can be seen from FIG. 12Error! Reference source not found. and FIG. 13, again representing examples 7b and 7f, resp. RMSEP values of ca. 0.1 to 0.3 mg were obtained by this method for all sets of cross-validation.

Figure 14:
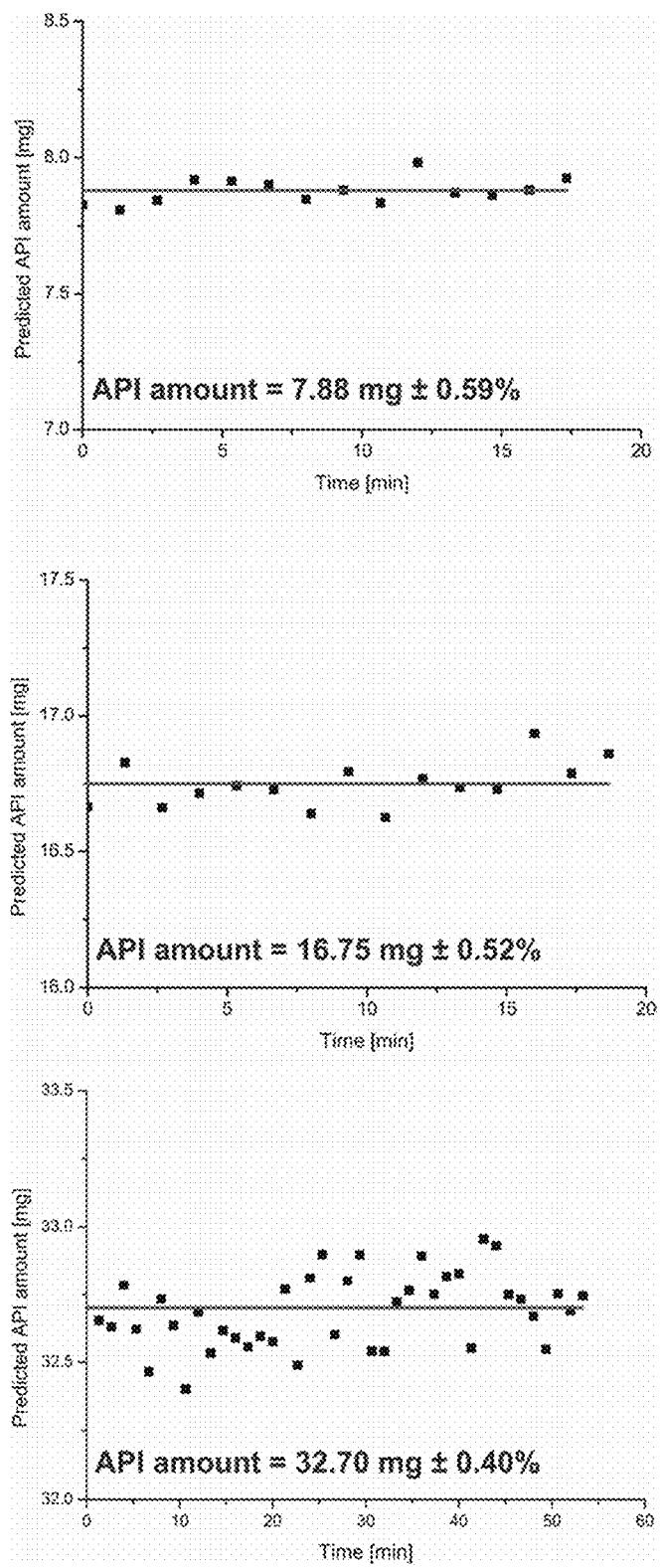
FIG. 14 is a plot of the results of a test of the intermediate precision of the Raman in-line measurements, performed by observing the Raman signal of tablets in a rotating coater drum without spraying for a period of time at different coating levels.

The intermediate precision of the Raman in-line measurements were investigated by observing the Raman signal of tablets in a rotating coater drum without spraying for a period of time at different coating levels. The relative standard deviation was found to be as low as ca. 0.4-0.6% as can be seen from FIG. 14.

Example 13

Comparison of in-line Process Monitoring Using Raman and NIR Methods

As reported in examples 7, 11, and 12 several batches have been manufactured under simultaneous Raman and NIR spectroscopic data recording. The endpoint of the coating process was however defined by a predefined amount of coating suspension that had to be sprayed onto the tablets in the coater (theoretical amount plus 1.0-2.5% overage to compensate losses during spraying). In addition, the weight gain of the tablets was monitored every 30 minutes.

The actual contents achieved by the selected method of endpoint determination (predefined amount of coating suspension) were compared to predicted contents under the assumption that a different method of endpoint determination would have been used (weight gain, Raman, NIR). The average results and the maximum observed deviation are also listed in the table. (Raman signals are available for seven out of the nine coating runs described in example 7a-i.)

| example no. | actual content [%] | predicted content (weight gain control) [%] | predicted content (NIR control) [%] | predicted content (Raman control) [%] |
|---|---|---|---|---|
| 7a | 100.5 | 91.0 | 103.3 | n.a. |
| 7b | 101.7 | 92.6 | 100.6 | 98.9 |
| 7c | 103.8 | 94.2 | 99.2 | 98.8 |
| 7d | 100.3 | 102.1 | 104.7 | 100.6 |
| 7e | 103.8 | 98.6 | 99.9 | n.a. |
| 7f | 101.9 | 92.5 | 100.1 | 102.3 |
| 7g | 101.2 | 92.8 | 100.6 | 99.9 |
| 7h | 100.1 | 97.2 | 99.6 | 99.9 |
| 7i | 102.2 | 95.3 | 99.5 | 101.2 |
| Average | 101.7 | 95.1 | 100.8 | 100.2 |
| maximum deviation | 3.8 | 9.0 | 4.7 | 2.3 |

As can be seen from the table, endpoint determination via defined amount of coating suspension to be sprayed assuming a relatively low spraying loss was suitable to meet the content target with a maximum deviation of ca. 4%. Obviously, an endpoint determination using the weight gain of the tablets would not improve the process but rather deteriorate. This is possibly due to water uptake during the coating process which cannot be differentiated from coating weight gain. On the other hand, applied to these batches, the NIR method would have improved the endpoint determination in average—with some exceptions where the results for a specific batch would be worse. Finally, the Raman method would have improved the endpoint determination in nearly all cases and in average pretty close to 100% and would have reduced the maximum deviation down to 2.3%.

Example 14

Colour Coating of Active Coated Tablets

The colour coating suspension was prepared via dispersion of the solid components in purified water. Preferably, ready-to-use film coating systems (such as Opadry II 85F230009 Orange, Opadry II 85F26912 Brown, and Opadry II 85F250022 Red) were dispersed purified water for at least 45 minutes using a dissolver stirrer.

A weighed amount of active coated tablets was introduced into a drum coater and pre-warmed until exhaust air has reached the predefined temperature, e.g. >40° C. Then, the colour coating suspension, was sprayed onto the moving tablet bed in the coater until the predefined amount of coating suspension (including 5-15% overage to compensate for spraying losses) has been used for spraying. Thereafter the tablets were polished in the drum without any further heating of the inlet air for at least further 10 minutes and until the exhaust air temperature had reached 35° C. whatever is longer.

The coating parameters were dependent on the scale and the equipment. Exemplary process parameters for several scales of drum coaters (all by L. B. BOHLE Maschinen+Verfahren GmbH, D-59320 Ennigerloh, corresponding dimensions are disclosed in examples 4, 5, 6 and 7) are listed in the table below:

| Coater | BFC 5 | BFC 5(10) | BFC 50 | BFC 400 |
|---|---|---|---|---|
| Drum load [kg] | 3-5 | 7-10 | 35-50 | 220-380 |
| Drum speed [rpm] | 14-20 | 12-16 | 10-14 | 6-10 |
| Air flow rate [m³/h] | 160 | 200-250 | 800-1200 | 2500-5000 |
| Inlet air temperature [° C.] | <60 | <60 | <60 | <60 |
| Exhaust air temperature [° C.] | 35-50 | 35-50 | 35-50 | 35-50 |
| Spray pressure (atomizing air) [bar] | 0.5-1 | 0.7-1.3 | 1.5-2.0 | 2.0-4.0 |
| Forming air pressure [bar] | 0.5-1 | 0.7-1.3 | 1.5-2.0 | 2.0-4.0 |
| Spraying rate [g/min] | 8-20 | 16-36 | 60-150 | 200-480 |

Typical spraying time: ca. 30 minutes-2 hours
Typical yield of spraying: 95.0-99.5%

The invention claimed is:

1. A process for the manufacture of tablets comprising a nifedipine in the core and candesartan cilexetil in the active coating layer with mean candesartan cilexetil content of 95-105%, comprising spraying an active coating suspension comprising candesartan cilexetil onto tablet cores comprising nifedipine using at least 4 spray nozzles until the desired amount of candesartan cilexetil has been applied to tablet cores as determined by in-line Raman spectroscopy.

2. The process of claim 1 wherein the in-line Raman spectroscopy is utilized using a PhAT probe and SNV preprocessed spectra in the spectral region from 1540 cm$^{-1}$ to 1750 cm$^{-1}$.

3. The process of claim 1, wherein the mean candesartan cilexetil content in the active coating layer is 98.5-101.5%.

4. The process of claim 1, wherein in-line Raman spectroscopy is used to determine the endpoint of the coating process, wherein the endpoint is determined by in-line Raman spectroscopy using a PhAT probe and SNV preprocessed spectra in the spectral region from 1540 cm$^{-1}$ to 1750 cm$^{-1}$.

5. The process of claim 1, wherein the candesartan cilexetil active coating process for each individual layer of the active coating comprises:
   a. providing a defined amount of tablet cores in a coating drum;
   b. pre-warming the tablet cores;
   c. spraying a coating suspension onto a moving tablet bed in the coating drum, thereby producing coated tablets;
   d. optionally further drying, polishing and/or cooling the coated tablets.

6. The process of claim 5 characterized in that the inter-tablet variability of the candesartan cilexetil content is less than 5%, characterized in that the spraying step is performed substantially continuously over at least 3 hours and optionally over two-fold of that time as a maximum spraying time.

7. The process of claim 5, wherein the peripheral speed of the coating drum exceeds 0.4 m/s.

8. The process of claim 5, wherein in that the spraying step is performed at a drum load of 60 to 90%.

9. The process of claim 5, wherein in step (b) the tablet cores are pre-warmed until the coated tablets or exhaust air has reached at least 40° C. as defined minimal temperature.

10. The process of claim 5, wherein in step (d) the coated tablets are dried, polished, and/or cooled until the coated tablets or exhaust air has reached 35° C. as defined maximal temperature.

11. The process of claim 5, wherein the spraying step is performed substantially continuously over at least 3 hours and optionally over 1.1 fold of that time as a maximum spraying time.

12. The process of claim 5, wherein the spraying step is performed substantially continuously over at least 6 hours.

13. The process of claim 5, wherein the peripheral speed of the coating drum exceeds 0.6 m/s.

* * * * *